United States Patent [19]

Christensen et al.

[11] 4,296,236

[45] Oct. 20, 1981

[54] 7-(OR 6-) SUBSTITUTED-7-(OR 6-)ACYLIMINO CEPHALOSPORIN (OR PENICILLIN) COMPOUNDS

[75] Inventors: Burton G. Christensen, Scotch Plains; David B. R. Johnston, Warren; Raymond A. Firestone, Fanwood, all of N.J.

[73] Assignee: Merck & Co., Inc., Rahway, N.J.

[21] Appl. No.: 539,881

[22] Filed: Jan. 9, 1975

Related U.S. Application Data

[62] Division of Ser. No. 243,057, Apr. 11, 1972, Pat. No. 3,875,146.

[30] Foreign Application Priority Data

| Apr. 30, 1971 | [GB] | United Kingdom | 13008/71 |
| Sep. 1, 1971 | [GB] | United Kingdom | 40813/71 |
| Sep. 1, 1971 | [GB] | United Kingdom | 40814/71 |
| Nov. 29, 1971 | [GB] | United Kingdom | 55232/71 |

[51] Int. Cl.$^3$ .................. C07D 499/02; C07D 501/14
[52] U.S. Cl. ..................................... 542/420; 544/21; 424/246; 424/270; 424/271; 260/245.2 R

[58] Field of Search ............ 260/243 C; 544/21; 542/420; 544/21; 424/246, 271, 270

[56] References Cited

U.S. PATENT DOCUMENTS

| 3,867,379 | 2/1975 | Dolfini et al. | 542/420 |
| 3,954,744 | 5/1976 | Dolfini et al. | 542/420 |
| 4,026,886 | 5/1977 | Dolfini et al. | 542/420 |
| 4,061,851 | 12/1977 | Dolfini et al. | 544/21 |
| 4,071,682 | 1/1978 | Dolfini et al. | 544/21 |

Primary Examiner—Nicholas S. Rizzo
Attorney, Agent, or Firm—Hesna J. Pfeiffer

[57] ABSTRACT

A process is provided which yields derivatives of cephalosporins and penicillins. The process starts with 7-aminodecephalosporanic acid or 6-APA and reacts with a carbonyl containing compound to form a Schiff's base (imino) adduct. This latter compound is then treated with a defined reactant yielding a novel Schiff's base adduct having a side chain on the carbon adjacent to the imino-nitrogen. The amino moiety can be regenerated and further reacted to form end compounds which are active against both gram-positive and gram-negative bacteria.

7 Claims, No Drawings

7-(OR 6-) SUBSTITUTED-7-(OR 6-)ACYLIMINO CEPHALOSPORIN (OR PENICILLIN) COMPOUNDS

This is a division of application Ser. No. 243,057 filed Apr. 11, 1972, now U.S. Pat. No. 3,875,146.

This invention relates to a new process for preparing new intermediate compounds known chemically as 7-aminodecephalosporanic acid having substituents at position-7. These compounds are used in preparing new and useful antibiotics. This process is also useful in preparing the analogous 6-substituted compounds in the penicillin series.

The compounds prepared by the process of this invention are the following:

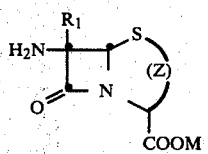

wherein (Z) is the group

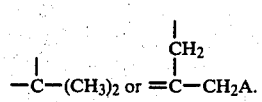

More specifically, the compounds can be described as the following: (the numbers indicate ring position):

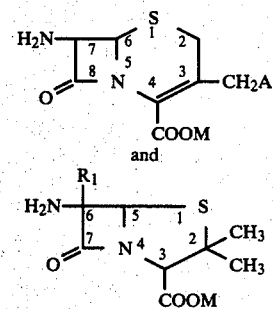

The nomenclature used in this application is further defined as follows. The compound,

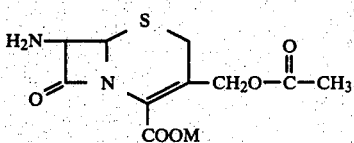

is called 7-aminocephalosporanic acid. The side chain at 3 is inherently contained in the name. By comparison, the skeleton

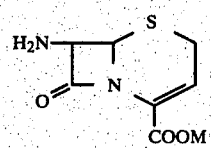

is called 7-aminodecephalosporanic acid. Derivatives of this compound which have substituents at 3- are named 7-amino-3-R-decephalosporanic acid.

In the above structural formulas, Compound IA is 7-amino-7-$R_1$-3-$CH_2$A-decephalosporanic acid, and Compound IB is 6-amino-6-$R_1$-penicillanic acid.

The substituents in Compounds I, IA, and IB are as follows: $R_1$ is lower alkyl, lower alkoxy, lower alkylthio, lower alkanoyl, lower haloalkoxy, lower haloalkylthio, halo, lower haloalkyl, lower alkanoyloxy, (α-hydroxy)lower alkyl, (α-hydroxy)lower alkenyl, β-substituted ethyl derivatives, allyl, benzyl, nitroso, carbamoyl carboloweralkoxy, sulfo, sulfamoyl, lower alkylsulfo, phospho, nitro, carboxy, dithiocarboxy, carbobenzoxy, or dimethylaminomethyl. These substituents are more specifically defined hereinafter.

The substituent A in Formula IA is hydrogen, hydroxy, fraio, mercapto, cyano, alkanoyloxy, alkanoylthio, aroyloxy, aroylthio, heteroaryloxy or heteroarylthio, the hetero ring having 5-6 members and having 1-3 hetero atoms, being O, S, or N or combinations thereof, azido, amino, carbamoyloxy, alkoxy, alkylthio, carbamoylthio, thiocarbamoyloxy, benzoyloxy, (p-chlorobenzoyl)oxy, (p-methylbenzoyl)oxy, pivaloyloxy, (1-adamantyl)carboxy, substituted amino such as alkylamino, dialkylamino, alkanoylamino, carbamoylamino, N-(2-chloroethylamino), 5-cyanotriazol-1-yl, 4-methoxycarbonyl-triazol-1-yl, or quaternary ammonium such as pyridinium, 3-methyl-pyridinium, 4-methyl-pyridinium, 3-chloro-pyridinium, 3-bromo-pyridinium, 3-iodo-pyridinium, 4-carbamoyl-pyridinium, 4-(N-hydroxymethylcarbamoyl)-pyridinium, 4-(N-carbomethoxycarbamoyl)pyridinium, 4-(N-cyanocarbamoyl)pyridinium, 4-(carboxymethyl)-pyridinium, 4-(hydroxymethyl)pyridinium, 4-(trifluoromethyl)pyridinium, quinolinium, picolinium, or lutidinium; N-loweralkylcarbamoyloxy, N,N-diloweralkylthiocarbamoyloxy, alkanoylcarbamoyloxy, hydroxyphenyl, sulfamoyloxy, alkylsulfonyloxy, or (cis-1,2-epoxypropyl)phosphono.

The substituent M in the above formulas can be an alkali metal, benzyl, alkanoyloxymethyl, alkylsilyl, phenalkanoyl, benzhydryl, alkoxyalkyl, alkenyl, trichloroethyl, hydrogen, benzoylmethyl, or methoxy.

Preferably, in the above Formulas I, IA, and IB, $R_1$ is lower alkyl, lower alkoxy, lower alkylthio, lower alkanoyl, lower haloalkoxy, lower haloalkylthio, halo, lower haloalkyl, or lower alkanoyloxy;

A is hydrogen, halo, azido, cyano, hydroxy, alkoxy, carbamoyloxy, thiocarbamoyloxy, N-loweralkylcarbamoyloxy, N,N-diloweralkylcarbamoyloxy, N-loweralkylthiocarbamoyloxy, N,N-diloweralkylthiocarbamoyloxy, alkanoyloxy, aroyloxy, mercapto, alkylthio, amino, alkylamino, alkanoylamino, hydroxyphenyl, sulfamoyloxy, quaternary ammonium, alkylsulfonyloxy, or (cis-1,2-epoxypropyl)phosphono;

and M is alkali metal, benzyl, alkylsilyl, diphenylmethyl, alkoxyalkyl, pivaloyloxymethyl, alkenyl, trichloroethyl, hydrogen, benzoylmethyl, or methoxybenzyl.

Even more preferably, $R_1$ is lower alkoxy, lower alkyl, lower alkylthio, lower haloalkoxy, lower haloalkylthio, halo, lower haloalkyl, or lower alkanoyloxy;

A is hydrogen, loweralkanoyloxy, heteroarylthio, carbamoyloxy, thiocarbamoyloxy, N-loweralkylcarbamoyloxy, N-loweralkylthiocarbamoyloxy, N,N-diloweralkylcarbamoyloxy, N,N-diloweralkylthiocarbamoyloxy, pyridinium, alkylpyridinium, halopyridinium, or aminopyridinium; and M is sodium, potassium, benzyl, benzhydryl, trimethylsilyl, trichloroethyl, methoxymethyl, hydrogen, benzoylmethyl, or methoxybenzyl.

Still more preferably, $R_1$ is lower alkoxy, lower alkyl, or halo;

A is hydrogen, loweralkanoyloxy, carbamoyloxy, N-loweralkylcarbamoyloxy, N,N-diloweralkylcarbamoyloxy, pyridinium, alkylpyridinium, halopyridinium, or aminopyridinium;

and M is sodium, potassium, trichloroethyl, benzyl, benzhydryl, methoxymethyl, or hydrogen.

It will be readily seen that other simple derivatives of the carboxylic acid functionality (COOM) can be easily prepared and would be obvious modifications of this invention. Many of such derivatives are described in the art. It is our intention that such derivatives should be considered as included within this invention, since they are readily available and easily determined by one skilled in the art. The only limitation for (M) is that it can be removed easily and does not interfere with the intervening reactions.

The processes of this invention can be schematically represented in the following flow sheets.

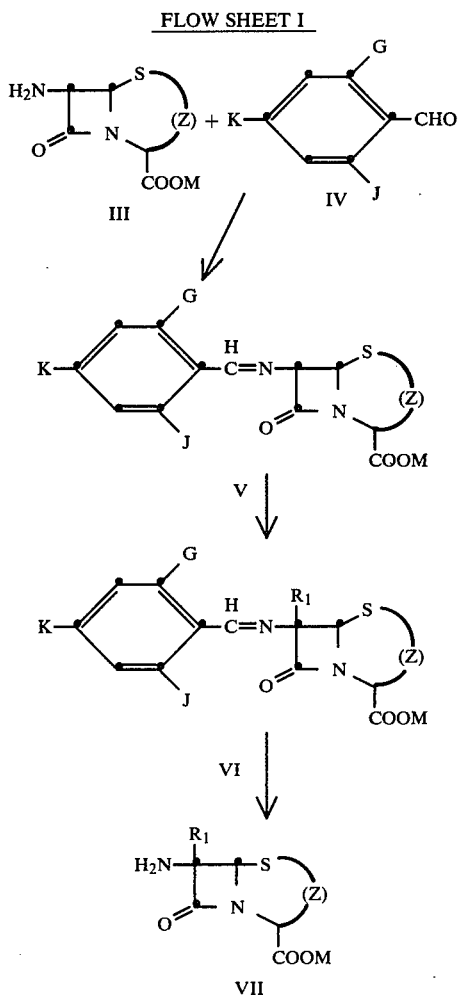

The basic inventive process can be summarized briefly as having three major steps: the first is the preparation of the imino derivative of the 6-(or 7-)amino group of penicillin or cephalosporin, respectively. This imino derivative is then substituted with the chosen reactant supplying the $R_1$ group desired. The specific reactant depends on the identity of the $R_1$ group. The third step is then the regeneration of the amino group.

Specifically, the starting material III is either 6-amino-penicillanic acid or 7-amino-decephalosporanic acid, and the esters thereof. "—Z—" is used in formula III to represent either the group

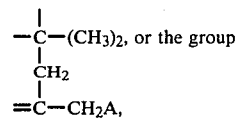

respectively, representing the penicillin or the cephalosporin structures. A and M are as defined above. The use of Z is appropriate since any of a great number of substituents can depend from that part of the ring, in both the penicillin and the cephalosporin series. The inventive process of this invention, involving as it does the carbon adjacent to the amino group, is not affected by the substituent at Z. One can readily see that the exemplary substituents of this application are illustrative only of preferred embodiments and that many other substituents can be employed.

The reactant IV employed in the first of the reaction is an aromatic aldehyde, optionally having at least one o- or p-electronegative substituent. In other words, at least one of J, G, and K may be a substituent selected from the group consisting of nitro, methyl, halo, sulfonyl, carboxyl derivatives such as esters or amides, cyano, and the like. The other two of J, G, and K can either be one of the above electronegative substituents, or hydrogen. The preferred reactants are p-nitrobenzaldehyde, where J=nitro, and G and H=hydrogen, and benzaldehyde.

Other carbonyl containing compounds, e.g., aldehydes and ketones such as acetone, hexafluoroacetone or chloral which will form stable imino derivatives will also be operable in this invention. Also, polycyclic aromatic aldehydes can be used, i.e., having 2–3 fused ring nuclei.

The starting material III and the aromatic aldehyde IV are mixed together in approximately equimolar amounts in an inert solvent. Suitable solvents are ethanol, dioxane, acetonitrile, dimethylformamide, dimethylsulfoxide, benzene, toluene, methylene chloride, chloroform, and the like. The reaction proceeds readily at temperatures ranging from ambient to reflux temperature of the solvent. Since this condensation is an equilibrium reaction and since water is one of the products of the reaction, water is removed from active participation in further reactions by any of a number of usual methods, including azeotropic distillation, molecular sieves, chemical entrapment using potassium carbonate, magnesium sulfate, etc., or borate esters. The particular method is dependent upon the exact parameters of the reaction. The reaction is terminated by evaporation of the solvent. The imino derivative V is then recovered and used in the next step.

The latter involves the substitution of the $R_1$ group at the carbon atom adjacent to the imino nitrogen. This reaction takes place in the presence of an inert solvent, such as those listed above, and in the additional presence of an activating agent which is an organic or inorganic base.

The activating agent can be any of a number of organic or inorganic bases. Tertiary (loweralkyl) amines are suitable, such as triethylamine, diisopropyl ethylamine; lower alkyl is used as having 1-4 carbon atoms and can be the same or different. Pyridine is also used. Lithium alkyls and lithium aryls, such as lithium alkyls having 1-4 carbon atoms, e.g., t-butyl lithium or phenyl lithium, could be used. Sodium hydride is also suitable.

The activating agent is added to the solution of compound V at a low temperature (−100° to 0° C. and preferably −100° to −60° C.) and under an inert atmosphere. The amount of activating agent employed is sufficient to produce a strong color change in the solution. The color is an indicator that the activated form of compound V is present.

The activated compound V is not isolated, but the next reagent is added directly to the reaction mixture.

The specific reagent which is employed in the reaction with the activated compound V to result in the substitution of the chosen $R_1$ group obviously depends on the $R_1$ group desired.

The following is of value in defining each reactant in terms of the final $R_1$ group.

TABLE 1

| Reactant | $R_1$ |
|---|---|
| 1. lower alkyl sulfate or halide | loweralkyl |
| 2. lower alkanoyl halide | loweralkanoyl |
| 3. lower alkyl peroxide | loweralkoxy |
| 4. haloloweralkyl peroxide | lowerhaloalkoxy |
| 5. loweralkyl disulfide or lower alkane sulfenyl halide | loweralkylthio |
| 6. haloloweralkyl disulfide | lowerhaloalkylthio |
| 7. tertbutylhypohalite or perhalomethylhypohalite or N-halosuccinimide or N-haloacetamide, or molecular halogen | halo |
| 8. dihaloloweralkane | haloloweralkyl |
| 9. loweralkanoyl peroxide | loweralkanoyloxy |
| 10. formaldehyde or loweralkyl-aldehyde | (α-hydroxy)loweralkyl |
| 11. reactive loweralkyl ketone | (α-hydroxy) branched loweralkyl |
| 12. reactive ethylene derivatives | (β-substituted)ethyl |
| 13. allyl halide | allyl |
| 14. benzyl halide | benzyl |
| 15. nitrosyl halide | nitroso |
| 16. carbamoyl halide | carbamoyl |
| 17. loweralkylhaloformate | carboloweralkoxy |
| 18. sulfuryl chloride | sulfo |
| 19. sulfamoylchloride | sulfamoyl |
| 20. loweralkylsufonyl halide | loweralkylsulfo |
| 21. phosphorus oxychloride | phospho |
| 22. acetone cyanohydrin nitrate | nitro |
| 23. carbon dioxide | carboxy |
| 24. carbon disulfide | dithiocarboxy |
| 25. haloformate | carbobenzoxy |
| 26. iodomethyltrimethylammonium iodide or bis-(dimethylamino) methane | dimethylaminomethyl |

The chosen reagent is added in an amount approximately equivalent to the moles of the activated compound V. The reaction proceeds immediately, as evidenced by a color change. The reaction mixture is then permitted to warm up to temperatures ranging from between 0° C. to ambient temperatures.

The terms used in Table I are elsewhere in the specification and are defined as follows:

"Loweralkyl" refers to an alkyl group having 1-6 carbon atoms.

"Loweralkanoyl" and "loweralkoxy" refer to a carbon chain of 1-6 carbon atoms.

"Halide", "halo", and "halite" are used to mean chlorine, bromine, fluorine, and iodine. Different halogens can be employed in the same moiety if more than one is indicated.

"Peroxide" indicates a compound having a —O—O— moiety.

"Disulfide" indicates a —S—S— moiety in a compound.

"Loweralkanoyl peroxide" is used to mean a compound of the formula

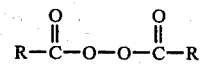

wherein R is loweralkyl having 1-6 carbon atoms.

"Loweralkyl aldehyde" is used to mean an aldehyde of the formula

wherein R is H or an alkyl group of 1-6 carbon atoms.

"(α-Hydroxy)lowerakyl" is used to mean a group of the formula

wherein R is hydrogen or alkyl having 1-6 carbon atoms.

"Reactive loweralkyl ketone" is used to mean a ketone of the formula

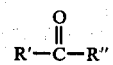

wherein one of R' and R" is a halogenated loweralkyl group, the halogen-substituted carbon being adjacent to the carbonyl function; or one of R' or R" is an alkyl carbonyl group. The carbonyl being adjacent to the carbonyl of the ketone; the other of R' or R" is loweralkyl. Thus, to illustrate, one type of "reactive loweralkyl ketone" is:

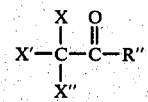

wherein X is halo, X" is halo or hydrogen, and X' is halo, hydrogen, or loweralkyl; and R" is loweralkyl. The other type is

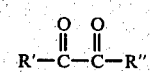

wherein R' is hydrogen or loweralkyl, and wherein R" is loweralkyl, haloloweralkyl, loweralkoxy, or haloloweralkoxy.

"(α-Hydroxy)branched loweralkyl" means a group of the formula

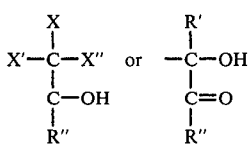

wherein X, X', X", R', and R" are as defined above.

"Reactive ethylene derivative" is used to mean an olefin which is activated by the presence of one or more strong electron with-drawing groups. For example, compounds of the formula CH$_2$=CHY where Y is

—NO$_2$, —CN,

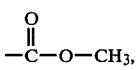

CF$_3$, SO$_2$R, RO$_3$R$_2$, and the like are included, wherein R is alkyl.

The term "(β-substituted)ethyl" is employed to mean the following group

—CH$_2$—CH$_2$Y wherein Y is the same as defined as above.

In addition to the processes outlined in Flow Sheet I, modifications are possible when R$_1$ is lower alkoxy, specifically, methoxy. These modifications are outlined in Flow Sheet II.

FLOW SHEET II

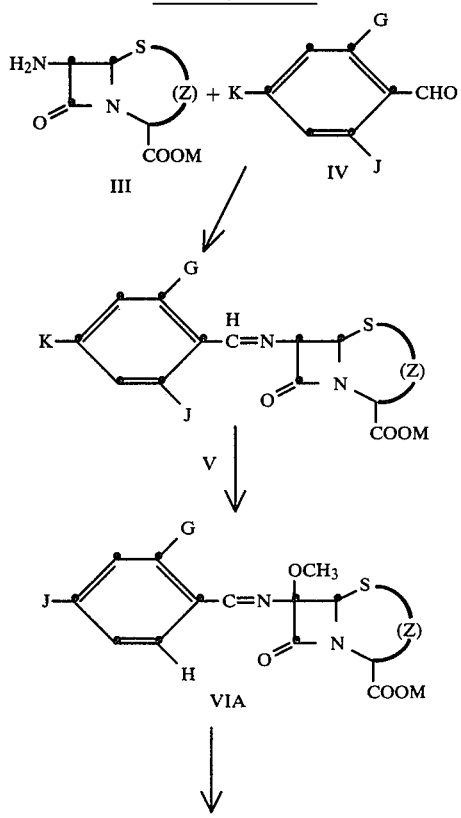

-continued
FLOW SHEET II

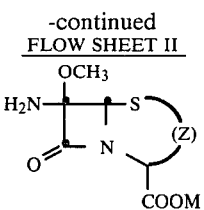

VIIA

Flow Sheet II is essentially identical to Flow Sheet I, except that the methoxy derivative is Compound VIA. The routes used to prepare Compound VIA involves the direct substitution of the methoxy group at the carbon atom adjacent to the imino nitrogen. This is the same route on Flow Sheet I, although certain specific reagents are added which yield the methoxy substituent. The reaction takes place in the presence of an inert solvent, such as those listed above, in the additional presence of the activating agent as defined above. This Route 1 is called the "direct methoxylation route" and the reagents can be dimethyl peroxide, methyl t-butyl peroxide, methylphenylsulfenate, o-methyldimethyl sulfoxonium methosulfate, or N-methoxy pyridinium methosulfate.

Once the novel compounds VI (Flow Sheet I) or VIA (Flow Sheet II) have been prepared, the imino moiety is converted to the amino moiety of compound VII as VIIA. Further discussion of this process will refer only to compound VII, since obviously VIIA is but one specific compound included within the generic compound VII.

The regeneration of VII from VI takes place by the reaction of VI with an amine in the presence of an acid catalyst. The amine employed can be aniline, hydrazine, or hydrazine derivatives such as phenylhydrazine, 2,4-dinitrophenyl hydrazine, and the like. The acid catalyst can be any commonly used strong organic or inorganic acid such as hydrochloric acid or p-toluene sulfonic acid. One preferable combination utilizes aniline hydrochloride, which serves as both acid and amine. Another preferred combination is 2,4-dinitrophenyl hydrazine and p-toluene sulfonic acid. The reaction conditions of the regeneration are chosen such that no undesired hydrolysis or ring damage occurs, and is preferably carried out in a lower alkanol medium (1–5 carbon atoms), such as methanol, ethanol, and the like, although other solvents including dimethoxyethane or dimethyl formamide may also be used. The temperature is that of the surroundings. The relative amounts of acid and amide employed depends on the specific aldehyde IV and amine used, since the regeneration involves an equilibrium. The choice of amounts of the reagents is within the skill of one in the art.

The novel compounds prepared in the reactions, which are compounds V and VI in Flow Sheet I, can be used to prepare valuable antibacterial agents useful against gram-positive and gram-negative bacteria. When the amino group of compound VII is acylated, the resulting products have enhanced activity against gram-negative organisms and also demonstrate resistance of β-lactamases. This activity includes effectiveness against many bacteria, including in vivo on *Proteus morganii* and, in addition, an effectiveness against the following gram-negative bacteria: *Escherichia coli, Proteus vulgaris, Proteus mirabilis, Salmonella schottmuelleri, Klebsiella pneumoniae AD, Klebsiella pneumoniae B,* and

*Paracolobactrum arizoniae*. Specific bactericidal activity is dependent upon the exact structure of the final product; not all compounds are active against all organisms.

The penicillin compound of formula VII, after acylation, can also be used to prepare active cephalosporins, using ring expansion techniques. These techniques can be briefly described: the sulfur atom in the penicillin compound is oxidized to the sulfoxide (S→O) valence state, using an oxidizing agent such as ozone or a peracid such as m-chloroperbenzoic acid, trifluoroperacetic acid, or the like. The penicillin 1-oxide thereby produced is then treated with an acid catalyst at an elevated temperature. The acid catalyst can be phosphoric acid, sulfuric acid, phosphonic acid, sulfonic acid, and their monoesters and organo derivatives. An inert solvent, preferably anhydrous, is also employed. A drying agent can be used if necessary to remove water. The reaction is conducted at a temperature between 75° C.-140° C., and preferably at the reflux temperature of the solvent. Following ring expansion, other manipulations can be made at positions 3 and 4 of the cephalosporin so that the desired active end product is obtained.

The starting materials used in this invention are prepared in accordance with known methods, see, e.g., Belgium Pat. No. 650,444 or U.S. Pat. No. 3,117,126, or using the following preparations.

In addition, the compounds of formula VI wherein $R_1$ is bromo can be used to prepare compounds wherein $R_1$ is methoxy. In other words, the 7-bromo or 6-bromo imino intermediates can be converted to 7-methoxy or 6-methoxy imino intermediates using methanol in the presence of a metal salt catalyst as the reagent. This conversion does not form a part of this invention, but is disclosed herein to demonstrate an additional utility for the brominated intermediate compounds. The process is claimed and described in U.S. Ser. No. 203,057, Christensen and Cama, filed November 29, 1971. The exact preparative method for the reaction is desired more fully infra.

In addition, referring again to Table I, we have found that when either t-butyl hydroperoxide or molecular oxygen are used as the reactant with activated Compound V, two novel intermediates are prepared. One is a nitrone,

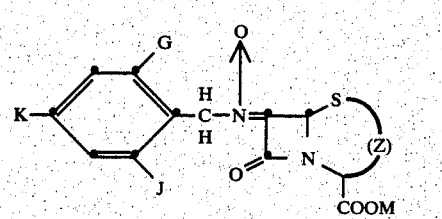

and the other is a dimer,

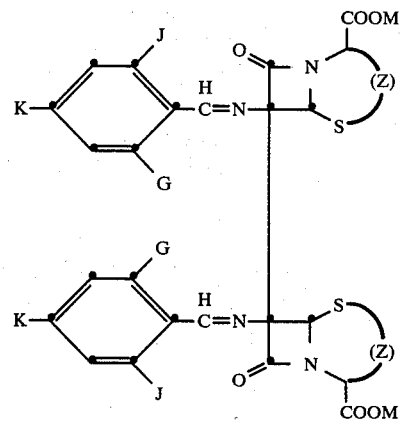

wherein M, K, G, J, and Z are as defined previously. These compounds can both be used to prepare active novel end-products. The nitrone of formula VIB can be used in reactions similar to those described in Table I, to substitute a desired substituent on the adjacent carbon atom, i.e., position 7 of the cephalosporin or position 6 of the penicillin nuclei. The N-oxy substituent can then be removed if desired. The reactions which are useful on a carbon adjacent to an N-oxy substituent are described in the literature, in addition to those reactions described herein. Following reaction of the nitrone VIB, the amino group can be regenerated as described; then acylated to yield desirable end products.

The dimer of Formula VIC can be converted to the di-amino dimer, and then the di-acylamino dimer, using reactions as described, to yield 6-penicillin-substituted penicillins or 7-cephalosporin-substituted-cephalosproins. These compounds are useful as anti-bacterial agents.

The acylamine moiety can be any of a number of substituents; generally, the final dimer product can be described by the formula:

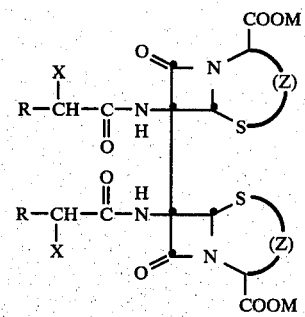

wherein Z and M are as defined above; and X is hydrogen, halo, amino, guanidino, phosphono, hydroxy, tetrazolyl, carboxyl, sulfo, or sulfamino; and R is phenyl, substituted phenyl, a monocyclic heterocyclic 5- or 6-membered ring containing one or more oxygen, sulfur, or nitrogen atoms in the ring, substituted heterocycles, phenylthio, heterocyclic, or substituted heterocyclic thio-groups, or cyano; the substituents on the R group being halo, carboxymethyl, guanidino, guanidino-methyl, carboxamidomethyl, aminomethyl, nitro, methoxy, or methyl. Preferably, X is hydrogen, amino, or carboxyl; and R is phenyl, or a 5-6 membered heterocyclic ring having 1-2 heteroatoms, the latter being either S, O, or N.

Still more preferably, X is hydrogen or carboxyl; and R is phenyl, or a 5-membered heterocyclic ring having one O or one S hetero atom.

The acyl group is reacted on the di-amino dimer, using a substituted acetyl halide or anhydride in the condensation reaction. This reactant can be described by the formula:

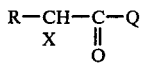
    IX wherein R and X are as defined, and Q is halo, preferably chloro or bromo, or the group

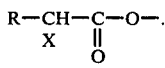

The substituted acetyl halide or anhydride IX is employed in molecular excess, and the reaction is conducted in an inert solvent at a temperature of between $-20°$ C. to ambient temperatures. The final product can be easily isolated by standard procedures, most suitably preparative thin-layer chromatography.

It is noted that when X in the above formulas is a reactive group such as carboxy, such as when the reactant is phenyl (α-carboxyacetyl)chloride, the group is blocked using, e.g., a carbobenzoxy substituent which can be removed easily following the condensation.

The blocking group on the acid functionality at position 4 of the cephalosporin ring or position 3 of the penicillin ring is then removed (to give M=hydrogen, sodium, or potassium) using methods available in the art, as a last step. For instance, the benzyl ester is removed by reduction effected most easily using catalytic hydrogenation; the benzhydryl group is readily cleaved by reaction with trifluoroacetic acid in the presence of anisole; any silyl ester can be removed by hydrolysis; the trichloro ethyl group is removed using zinc in acetic (or similar) acid.

PREPARATION 1

3-Carbamoyloxymethyl-7-Aminodecaphalosporanic Acid

7-Aminocephalosporanic acid is reacted with t-butoxycarbonylazide to produce the 7β-(t-butoxycarbonyl) derivative in accordance with known methods. This derivative is then intimately contacted with citrus acetylesterase in aqueous phosphate buffer at pH 6.5–7 for 15 hours and 3-hydroxymethyl 7β-(t-butoxycarbonyl)aminodecephalosporanic acid is recovered from the resulting reaction mixture.

To 0.2 g. of 3-hydroxymethyl 7β-(t-butoxycarbonyl)aminodecephalosporanic acid suspended in 5 ml. of acetonitrile, cooled to 0° C. and maintained under nitrogen atmosphere is added 0.15 ml. of chlorosulfonyl isocyanate. The reaction mixture is stirred for 70 minutes and then evaporated under diminished pressure to dryness. The resulting residue is taken up in 10 ml. of ethylacetate and 10 ml. of 0.1 N phosphate buffer. The pH of the aqueous layer is adjusted to about 1.6 and the mixture stirred for 2½ hours at room temperature. The pH is then adjusted to about 8 with aqueous tripotassium phosphate solution, and the aqueous phase is separated. The organic phase is re-extracted with 10 ml. of phosphate buffer at pH 8. The combined aqueous phase is adjusted to pH 2.1 with hydrochloric acid and extracted twice with ethylacetate. The ethylacetate extractions are dried over sodium sulfate and evaporated under diminished pressure to afford 0.055 g. of residue. This residue is washed with ether to afford 3-carbamoyloxymethyl 7β-(t-butoxycarbonyl)aminodecephalosporanic acid which is recovered as a yellow solid.

3-Carbamoyloxymethyl 7β-(t-butoxycarbonyl)aminodecephalosporanic acid (0.5 g.) in 3.5 ml. of anisole is stirred with 2 ml. of trifluoroacetic acid at 0° C. for 5 minutes. The resulting reaction mixture is evaporated under reduced pressure to afford 3-carbamoyloxymethyl-7-aminodecephalosporanic acid which is purified further by crystallization from water at pH 2.

PREPARATION 2

3-Hydroxymethyl-7-Aminodecephalosporanic Acid

The 3-hydroxymethyl-7-aminodecephalosporanic acid is obtained as the lactone by acid hydrolysis of cephalosporin C in accordance with procedures known in this art.

PREPARATION 3

Trimethylsilyl 3-Carbamoyloxymethyl-7-Aminodecephalosporanate

A mixture of 0.5 mg. of 3-carbamoyloxymethyl-7-aminodecephalosporanic acid, 2 ml. of hexamethyldisilazane and 8 ml. of chloroform is stirred overnight at reflux temperature protected from moisture. The solvent and excess hexamethyldisilazane are removed at reduced pressure, leaving a residue containing trimethylsilyl 3-carbamoyloxymethyl-7-aminodecephalosporanate.

PREPARATION 4

3-Pyridiniummethyl-7-Aminodecephalosporanic Acid

This compound is prepared by treating cephalosporin C with pyridine followed by acid hydrolysis as described in U.S. Pat. No. 3,117,126.

PREPARATION 5

3-Methyl-7-Aminodecephalosporanic Acid

This compound is prepared from cephalosporin C by catalytic reduction followed by hydrolytic removal of the 5-aminodipoyl side chain as described in U.S. Pat. No. 3,129,224.

PREPARATION 6

3-Chloromethyl-7-Aminodecephalosporanic Acid

This compound is prepared from the 3-methyl compound by reaction with chlorine gas. The bromomethyl or iodomethyl derivatives can be prepared from the 3-hydroxymethyl compound by reaction with phosphorus tribromide or phosphorus triiodide, respectively.

This invention can be further illustrated by the following examples.

EXAMPLE 1

7-Aminocephalosporanic Acid Benzhydryl Ester

272 Mg. of 7-aminocephalosporanic acid is slurried 5 min. at 25° C. in 7 ml. dioxane with 170 mg. p-toluenesulfonic acid.H₂O. Methanol (2 ml.) is added, the solvents are removed in vacuo, and dioxane is twice added and evaporated in vacuo. Dioxane (8 ml.) is added, and then 290 mg. diphenyldiazomethane. After the evolution of nitrogen is complete, the solvent is distilled in vacuum, and the residue stirred with methylene chloride (10 ml.) and water (10 ml.) containing sufficient $K_2HPO_4$ to bring the pH to 8. The layers are separated and the aqueous portion extracted twice more with $CH_2Cl_2$. The combined organic layers are dried with sodium sulfate, filtered and evaporated, leaving oily crystals. Washing with ether affords a dry solid, 150 mg. (35%), m.p. 110°–115° C. which is the product, 7-aminocephalosporanic acid benzhydryl ester.

In a like manner, the benzhydryl and other esters of 3-methyl-7-aminodecephalosporanic acid, 3-chloromethyl-7-aminodecephalosporanic acid, 3-carbamoyloxymethyl-7-aminodecephalosporanic, and 3-pyridiniummethyl-7-aminodecephalosporanic acid can be prepared.

EXAMPLE 2

7-(p-Nitrobenzylideneamino)Cephalosporanic Acid Benzhydryl Ester

A mixture of 438 mg. of benzhydryl 7-aminocephalosporanate and 151 mg. of p-nitrobenzaldehyde in 5 ml. of methylene chloride containing 0.2–0.5 g. magnesium sulfate is stirred at ambient temperature for 0.5 hours, filtered, and evaporated under reduced pressure. The product, identified by nmr as the p-nitrobenzylideneamino derivative is used in the next step without further purification.

In a like manner, the following imino derivatives can be made: 7-(p-methylsulfonylbenzylideneamino)cephalosporanic acid benzhydryl ester; 7-(o-nitrobenzylideneamino)cephalosporanic acid benzhydryl ester; 7-(o,p-dinitrobenzylideneamino)cephalosporanic acid benzhydryl ester; 7-(p-cyanobenzylideneamino)cephalosporanic acid benzhydryl ester; and 7-(p-benzylideneamino)cephalosporanic acid benzhydryl ester; using the following aromatic aldehydes, respectively; p-methylsulfonylbenzaldehyde, o-nitrobenzaldehyde, o,p-dinitrobenzaldehyde, p-cyanobenzaldehyde, and benzaldehyde.

The other esters prepared in Example 1 can also be reacted to form the imino derivatives using the above procedure.

EXAMPLE 3

7-(p-Nitrobenzylideneamino)-7-Methyl-Cephalosporanic Acid Benzhydryl Ester

Benzhydryl 7-(p-nitrobenzylideneamino)cephalosporanate, 286 mg. is dissolved in 8 ml. dry tetrahydrofuran. At −78° C. under a nitrogen atmosphere, 0.218 ml. of 2.3 M phenyl lithium is added. Subsequently, a solution of 0.4 ml. of methyliodide in 10 ml. of DMF is added. The reaction mixture is allowed to warm to room temperature over ½ hour. The mixture is added to 100 ml. benzene and washed successively with water three times, aqueous pH 2 phosphate buffer, water, and pH 8 phosphate buffer. After drying, filtering and removing the solvent, the crude product, weighing 330 mg., is recovered. Characterization by NMR and IR yields the following peaks: NMR: 1.8δ, (7α-methyl), 1.9δ (acetyl), 3.3, 3.4δ (SCH$_2$), 4.7, 4.8δ (CH$_2$OAc), 4.8δ (6α-H), 6.9δ (CHφ$_2$), 8.65δ (CH=N), 7.2–8.2δ (aromatics). IR: β-lactam and ester carbonyls at 5.64 and 5.74μ respectively. The product is identified as 7-(p-nitrobenzylideneamino)-7-methyl-cephalosporanic acid benzhydryl ester.

Benzhydryl 7-ethyl-7-(p-nitrobenzylideneamino)-cephalosporanate is prepared in a like manner using 143 mg. of benzhydryl 7-(p-nitrobenzylideneamino)cephalosporanate in 2 ml. of tetrahydrofuran at −78° C. under nitrogen. A solution of 0.8 ml. ethyliodide in 10 ml. hexamethylphosphoramide is added over 4 minutes at −78° C. The mixture is allowed to warm to room temperature, then is diluted with 50 ml. of benzene and washed as above. After drying with MgSO$_4$, filtration, and evaporation of the solvent, crude benzhydryl 7-ethyl-7-(p-nitrobenzylideneamino)cephalosporanate is recovered. Characterization yields the following data: NMR: 1.08δ, t; 2.16δ, q; J=7 Hz (7α-ethyl), 1.97δ (acetyl), 3.03, 3.34, 3.41, 3.71δ (SCH$_2$), 4.95δ (6α-H), 4.53, 4.76, 4.89, 5.11δ (CH$_2$OAc), 6.95δ (CHφ$_2$), 8.82δ (CH=N), 7.2–8.2δ (aromatics). IR: 5.65μ (β-lactam), 5.74μ (ester).

In a like manner, the other 7-loweralkyl derivatives can be prepared. Using methyl sulfate, isopropyl sulfate, butyl sulfate, pentyl sulfate, or hexyl sulfate, respectively, the compounds 7-(p-nitrobenzylideneamino)-7-methyl-cephalosporanic acid benzhydryl ester, 7-(p-nitrobenzylideneamino)-7-isopropylcephalosporanic acid benzhydryl ester, 7-(p-nitrobenzylideneamino)-7-butyl-cephalosporanic acid benzhydryl ester, 7-(p-nitrobenzylideneamino)-7-pentyl-cephalosporanic acid benzhydryl ester, and 7-(p-nitrobenzylideneamino)-7-hexyl-cephalosporanic acid benzhydryl ester, respectively, are prepared.

In addition, the 7-loweralkyl derivatives of the imino compounds prepared in Example 2 can be easily synthesized using this reaction.

Also, in an analogous manner, 7-(p-nitrobenzylideneamine)-7-cephalosporanic acid benzhydryl ester or 7-(p-nitrobenzylideneamino)-7-benzyl-cephalosporanic acid benzhydryl ester can be prepared using allyl iodide or benzyl iodide, respectively.

EXAMPLE 4

7-(Benzylideneamino)-7-Methoxy-3-Carbamoyloxymethyldecephalosporanic Acid Benzhydryl Ester Benzhydryl 7-(benzylideneamino)-3-carbamoyloxymethyldecephalosporanate as prepared in Example 2, 527 mg., is dissolved in 20 ml. dry tetrahydrofuran. At −78° C., under nitrogen, 0.435 ml. of 2.3 M phenyl lithium is added. Bis(methyl)peroxide, 62 mg., is then added and then the reaction mixture is allowed to warm to room temperature over a one hour period. Benzene, 150 ml., containing 0.1 ml. acetic acid is added and the mixture washed with water, dried with MgSO$_4$, filtered and evaporated, providing the crude product. These are separated by chromatography on silica gel, eluting with 25:1 chloroform-ethyl acetate. The desired product, 7-(benzylideneamino)-7-methoxy-3-carbamoyloxymethyldecephalosporanic acid benzhydryl ester, is identified.

In a like manner, 104 mg. of methyl t-butyl peroxide, 140 mg. of methyl phenyl sulfenate, or 221 mg. of N-methoxy pyridinium methosulfate can be used in place of the dimethyl peroxide to prepare the 7-methoxy compounds.

In a like manner, the following loweralkyl peroxide can be used to prepare the other 7-loweralkoxy derivatives. For instance, bis(ethyl)peroxide, bis(isopropyl)peroxide, and bis(pentyl)peroxide, respectively, yield 7-(p-nitrobenzylideneamino)-7-ethoxy-cephalosporanic acid benzhydryl ester; 7-(p-nitrobenzylideneamino)-7- isopropoxy-cephalosporanic acid benzhydryl ester; and 7-(p-nitrobenzylideneamino)-7-pentoxy-cephalosporanic acid benzhydryl ester, respectively.

In a like manner, using the following bis(loweralkyl)-disulfides can be used to prepare the analogous loweralkylthio derivatives. For instance, bis(methyl)disulfide, bis(ethyl)disulfide, bis(isopropyl)disulfide, and bis(n-butyl)disulfide, respectively, yield 7-(p-nitrobenzylideneamino)-7-methylthio-cephalosporanic acid benzhydryl ester; 7-(p-nitrobenzylideneamino)-7-ethylthio-cephalosporanic acid benzhydryl ester; 7-(p-nitrobenzylideneamino)-7-isopropylthio-cephalosporanic acid benzhydryl ester; and 7-(p-nitrobenzylideneamino)-7-n-butylthio-cephalosporanic acid benzhydryl ester, respectively.

The loweralkylthio compounds of this example can also be prepared using loweralkane sulfenyl chloride as the reagent. The reagent, e.g., methane sulfenyl chloride, is prepared from chlorine and methyldisulfide using the procedure of Douglass et al, *J. Org. Chem.* 25, 221 (1960). After preparation and distillation, a normal solution in tetrahydrofuran is prepared. 200 Mg. of benzhydryl 7-(p-nitrobenzylideneamino)cephalosporanate is then treated with 0.2 ml. of 2.3 M phenyl lithium at −78° C. in 2.0 ml. tetrahydrofuran. An equivalent of the methane sulfenyl chloride solution is added dropwise. As the reaction is completed, the color lightens sharply. The reaction mixture is allowed to warm to room temperature and is then quickly evaporated to a gum under reduced pressure. The gum is taken up in benzene and washed successively with dipotassium hydrogen phosphate solution, sodium dihydrogen phosphate solution, water and finally dried with magnesium sulfate. After filtration and evaporation under reduced pressure, the resultant gum is flushed several times with carbon tetrachloride, and then purified by preparative tlc on four 1000μ 8″×8″ silica plates, developed with 5% ethyl acetate in chloroform. The desired material, which is 7-(p-nitrobenzylideneamino)-7-methylthio-cephalosporanic acid benzhydryl ester, after isolation amounts to 57.4 mg. The nmr spectrum in CDCl$_3$ shows peaks of 525 (1 H), 495, 487, 434, 468 ( 4 H), 437 (5 H), 370 (1 H) 308, 295, 288, 274 (2 H), 304 (1 H), 225, 207, 203, 184 (2 H), 135 (3H), 119 (3 H) in cps, measured downfield from tms.

EXAMPLE 5

7-(Benzylideneamino)-7-Methoxy-3-Carbamoyloxymethyldecephalosporanic Acid Benzhydryl Ester Benzhydryl 7-(benzylideneamino)-3-carbamoyloxymethyldecephalosporanate, 527 mg., is dissolved in 20 ml. dry tetrahydrofuran. At −78° C., under nitrogen, 0.435 ml. of 2.3 M phenyl lithium is added. The reaction mixture is allowed to rise in temperature to −50° C. Then freshly prepared o-methyl dimethyl sulfoxonium methosulfate, (CH$_3$)$_2$S$^+$OCH$_3$O$^-$SO$_2$CH$_3$, in 1:1 DMSO: hexamethylphosphoramide is added. This reagent is prepared as follows: Dimethyl sulfate, 252 mg., is dissolved in 25 ml. dry DMSO and allowed to react at room temperature for 3 hours. To this solution is added 25 ml. hexamethylphosphoramide (HMPA), and the mixture is then added to the reaction mixture, supra. The methoxylation reaction mixture is stirred for 10 minutes at −50° C. and then allowed to warm to room temperature. Benzene, 200 ml., is added, and the solution washed six times with water, dried with MgSO$_4$, filtered and evaporated, affording the product, 7-(benzylideneamino)-7-methoxy-3-carbamoyloxymethyldecephalosporanic acid benzhydryl ester.

EXAMPLE 6

7-(p-Nitrobenzylideneamino)-7-(2,2,2-Trichloroethoxycarbonyl)Cephalosporanic Acid Benzhydryl Ester Benzhydryl 7-(p-nitrobenzylideneamino)cephalosporanate, 146 mg. in 4 ml. tetrahydrofuran, is cooled to −78° C. under nitrogen. Phenyl lithium, 1 equivalent (0.109 ml. of 2.3 M) is added, followed by 1 equivalent (0.034 ml.) trichloroethoxycarbonyl chloride. The mixture is stirred out of the cooling bath until it reaches room temperature. Benzene, 50 ml., is added and the solution is washed successively with aqueous pH 2 phosphate buffer, water, and aqueous pH 8 phosphate buffer. The solution is dried with MgSO$_4$, filtered and evaporated, affording 7-(p-nitrobenzylideneamino)7-(2,2,2-trichloroethoxycarbonyl)-cephalosporanic acid benzhydryl ester.

In a like manner, the other 7-loweralkanoyl derivatives can be prepared. Using propionyl chloride, i-butyryl bromide, valeryl chloride, or caproyl bromide, respectively, the compounds 7-(p-nitrobenzylideneamino)-7-propionyl-cephalosporanic acid benzhydryl ester, 7-(p-nitrobenzylideneamino)-7-i-butyryl-cephalosporanic acid benzhydryl ester, 7-(p-nitrobenzylideneamino)-7-valeryl-cephalosporanic acid benzhydryl ester, and 7-(p-nitrobenzylideneamino)-7-caproyl-cephalosporanic acid benzhydryl ester, respectively, are prepared.

In a like manner, the compounds 7-(p-nitrobenzylideneamino)-7-nitroso-cephalosporanic acid benzhydryl ester; 7-(p-nitrobenzylideneamino)-7-carbamoyl-cephalosporanic acid benzhydryl ester; 7-(p-nitrobenzylideneamino)-7-carboethoxy-cephalosporanic acid benzhydryl ester; 7-(p-nitrobenzylideneamino)-7-sulfo-cephalosporanic acid benzhydryl ester; 7-(p-nitrobenzylideneamino)-7-sulfamoyl-cephalosporanic acid benzhydryl ester; 7-(p-nitrobenzylideneamino)-7-methylsulfo-cephalosporanic acid benzhydryl ester; 7-(p-nitrobenzylideneamino)-7-phospho-cephalosporanic acid (benzhydryl ester; or 7-(p-nitrobenzylideneamino)-7-nitro-cephalosporanic acid benzhydryl ester can be prepared using the reagents nitrosyl, chloride, carbamoyl chloride, ethyl chloroformate, sulfonyl chloride, methanesulfonyl chloride, phosphorus oxychloride, or acetone cyanhydrin nitrate, respectively. The latter reagent has the formula:

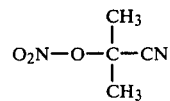

EXAMPLE 7

7-(p-Nitrobenzylideneamino)-7-TrifluoromethoxyCephalosporanic Acid Benzhydryl Ester Benzhydryl 7-(p-nitrobenzylideneamino)cephalosporanate as prepared in Example 2, 571 mg., is stirred at 0° C. under nitrogen in 10 ml. acetonitrile. Bis(trifluoromethyl)peroxide, 170 mg., is added and then, over a one hour period, 387 mg. diisopropylethylamine in 5 ml. acetonitrile.

The reaction mixture is evaporated in vacuo, taken up in 25 ml. benzene, filtered, and washed successively with water, dilute phosphoric acid (buffered at pH 2), water and aqueous bicarbonate. The solution is dried with MgSO₄, filtered and evaporated, providing the crude product as a mixture of epimers at C-7. These are separated by chromatography on silica gel, eluting with 4:1 chloroform-ethyl acetate. The desired product 7-(p-nitrobenzylideneamino)-7-trifluoromethoxy-cephalosporanic acid benzhydryl ester, is identified.

In a like manner, bis(trifluoromethyl)disulfide can be used to prepare the 7-(p-nitrobenzylideneamino)-7-trifluoromethylthio-cephalosporanic acid benzhydryl ester.

In addition, the 7-haloloweralkoxy derivatives of the other imino compounds prepared in Example 2 can be easily synthesized using this reaction.

EXAMPLE 8

7-(p-Nitrobenzylideneamino)-7-Chlorocephalosporanic Acid Benzhydryl Ester 7-(p-Nitrobenzylideneamino)-cephalosporanic acid benzhydryl ester, prepared as in Example 2, 527 mg., in tetrahydrofuran is cooled to −78° C. under nitrogen. One equivalent of phenyl lithium is added, followed by the addition of 109 mg. of t-butyl hypochlorite. The inky blue color is quenched to a medium pale brown color following addition of the latter reagent. After 25 seconds, 1 ml. of tetrahydrofuran containing 0.1 ml. water and 0.1 ml. acetic acid is added, followed by 100 ml. benzene. Most of the solvent is evaporated in vacuo, 50 ml. of benzene added and the solution washed with aqueous pH 2 phosphate buffer, water, and aqueous pH 8 phosphate buffer. After drying with MgSO₄, filtration and evaporation of the solvent, the residue is identified as containing benzhydryl 7-chloro-7β-(p-nitrobenzylideneamino)cephalosporanate.

The compound, 7-(p-nitrobenzylideneamino)-7-bromo-cephalosporanic acid benzhydryl ester is prepared in the same manner using t-butyl hypobromite.

In an analogous process, the reagent trifluoromethylhypofluorite reacts with 7-(p-nitrobenzylideneamino)-cephalosporanic acid benzhydryl ester to yield 7-(p-nitrobenzylideneamino)-7-fluoro-cephalosporanic acid benzhydryl ester.

In addition, the 7-halo derivatives of the other imino compounds prepared in Example 2 can be easily synthesized using this reaction.

EXAMPLE 9

Benzhydryl 7-(Benzylideneamino)-7-Methoxy-3-Carbamoyloxymethyl Decephalosporanate (via 7-Bromo Intermediate)

A. 3-Carbamoyloxymethyl-7-Aminodecephalosporanic Acid

7-Aminocephalosporanic acid is treated with t-butoxycarbonylazide to produce the 7β-(t-butoxycarbonyl) derivative in accordance with known methods. This derivative is then intimately contacted with citrus acetylesterase in aqueous phosphate buffer at pH 6.5–7 for 15 hours and 3-hydroxymethyl 7β-(t-butoxycarbonyl)aminodecephalosporanic acid is recovered from the resulting reaction mixture.

To 0.2 g. of 3-hydroxymethyl 7β-(t-butoxycarbonyl)aminodecephalosporanic acid suspended in 5 ml. of acetonitrile, cooled to 0° C. and maintained under nitrogen atmosphere is added 0.15 ml. of chlorosulfonyl isocyanate. The reaction mixture is stirred for 70 minutes and then evaporated under diminished pressure to dryness. The resulting residue is taken up in 10 ml. of ethylacetate and 10 ml. of 0.1 N phosphate buffer. The pH of the aqueous layer is adjusted to about 1.6 and the mixture stirred for 2½ hours at room temperature. The pH is then adjusted to about 8 with aqueous tripotassium phosphate solution, and the aqueous phase is separated. The organic phase is re-extracted with 10 ml. of phosphate buffer at pH 8. The combined aqueous phase is adjusted to pH 2.1 with hydrochloric acid and extracted twice with ethylacetate. The ethylacetate extractions are dried over sodium sulfate and evaporated under diminished pressure to afford 0.055 g. of residue. This residue is washed with ether to afford 3-carbamoyloxymethyl-7β-(t-butoxycarbonyl)aminodecephalosporanic acid which is recovered as a yellow solid.

3-Carbamoyloxymethyl-7β-(t-butoxycarbonyl)aminodecephalosporanic acid (0.5 g.) in 3.5 ml. of anisole is stirred with 2 ml. of trifluoroacetic acid at 0° C. for 5 minutes. The resulting reaction mixture is evaporated under reduced pressure to afford 3-carbamoyloxymethyl-7-aminodecephalosporanic acid which is purified further by crystallization from ethylacetate.

B. 7-Amino-3-Carbamoyloxymethyldecephalosporanic Acid Benzhydryl Ester 0.020 grams of 7-amino-3-carbamoyloxymethyldecephalosporanic acid is slurried 5 min. at 25° C. in 7 ml. dioxane with 170 mg. p-toluenesulfonic acid.H₂O. Methanol (2 ml.) is added, the solvents are removed in vacuo, and dioxane is twice added and evaporated in vacuo. Dioxane (8 ml.) is added, and then 290 mg. diphenyldiazomethane. After the evolution of nitrogen is complete, the solvent is distilled in vacuum, and the residue stirred with methylene chloride (10 ml.) and water (10 ml.) containing sufficient K₂HPO₄ to bring the pH to 8. The layers are separated and the aqueous portion extracted twice more with CH₂Cl₂. The combined organic layers are dried with sodium sulfate, filtered and evaporated, leaving oily crystals. Washing with ether affords a dry solid, the product, 7-amino-3-carbamoyloxymethyldecephalosporanic acid benzhydryl ester.

C. 7-(Benzylideneamino)-3-Carbamoyloxymethyldecephalosporanic Acid Benzhydryl Ester The 7-amino-3-carbamoyloxymethyldecephalosporanic acid benzhydryl ester, as prepared in Step B, 439 mg., is refluxed one hour in 50 ml. benzene with 106 mg. benzaldehyde in an azeotropic drying apparatus. The solvent is vacuum distilled away, leaving 527 mg. of product which is used in the next step without further purification. Samples which are identified show the structure to be the 7-(benzylideneamino)-3-carbamoyloxymethyldecephalosporanic acid benzhydryl ester.

D. Benzhydryl 3-Carbamoyloxymethyl-7-Bromo-7-Benzylideneaminodecephalosporanate

Benzhydryl 7-(benzylideneamino)-3-carbamoyloxymethyldecephalosporanate, 527 mg., is dissolved in 20 ml. dry tetrahydrofuran. At −78° C., under nitrogen, 0.435 ml. of 2.3 M phenyl lithium is added. The reaction mixture is stirred at −78° C. for 5 minutes. 0.2 Grams of N-bromosuccinimide in 3 ml. of anhydrous tetrahydrofuran is then added. The cooling bath is removed and the reaction mixture allowed to come to 0° C. The solvent is removed under reduced pressure and the residue taken up in methylene chloride (30 ml.) and washed with pH 7 phosphate buffer, and then with water, dried, and evaporated to a volume of about 12 ml. This solution of benzhydryl 3-carbamoyloxymethyl-7-bromo-7-benzylideneaminodecephalosporanate is not further characterized but used directly in the next step. In a like manner, N-bromo acetamide or molecular bromine can be used to prepare the same compound.

E. Benzhydryl 3-Carbamoyloxymethyl-7-Benzylideneamino-7-Methoxydecephalosporanate 0.200 G. of silver oxide is suspended in 20 ml. of methanol. The solution of the 7-bromo-7-benzylideneamino derivative obtained in Step A is added dropwise over 10 minutes to the silver oxide suspension. The reaction mixture is stirred for another 15 minutes. The silver salts are removed by filtration, the filtrate evaporated, and the residue taken up in benzene and evaporated to give the benzhydryl 3-carbamoyloxymethyl-7benzylideneamino-7-methoxydecephalosporanate as an oil.

EXAMPLE 10

7-(p-Nitrobenzylideneamino)-7-DifluoromethylCephalosporanic Acid Benzhydryl Ester Benzhydryl 7-(p-nitrobenzylideneamino)cephalosporanate prepared as in Example 2, 571 m.g, is dissolved in 20 ml. 1,2-dimethoxyethane (DME) containing 1 ml. chlorodifluoromethane. With vigorous stirring under nitrogen, 112 mg. potassium t-butoxide is slowly introduced as a slurry in DME over about one hour.

After stirring an additional hour, KCl is filtered off and the volatiles removed in vacuo, leaving behind crude product suitable for use in the next step.

It may be purified, if desired by chromatography on silica gel, eluting with 2% ethyl acetate in chloroform. The pure product is identified as 7-(p-nitrobenzylideneamino)-7-difluoromethylcephalosporanic acid benzhydryl ester.

In addition, the 7-haloloweralkyl derivatives of the other imino compounds prepared in Example 2 can be easily synthesized using this reaction.

EXAMPLE 11

7β-(p-Nitrobenzylideneamino)-7α-Acetoxycephalosporanic Acid Benzhydryl Ester

Benzhydryl 7-(p-nitrobenzylideneamino)-cephalosporanate prepared as in Example 2, 571 mg., is stirred at 0° C. under nitrogen in 10 ml. acetonitrile. Acetyl peroxide, 118 mg., is introduced, followed by 129 mg. diisopropylethylamine, which is added in acetonitrile over a 5 min. period.

The reaction mixture is aged 5 min. at room temperature and evaporated in vacuo. The residue is taken up in 25 ml. benzene and washed successively with water, dilute phosphoric acid (buffered at pH 2), water, and aqueous bicarbonate. The solution is dried with $MgSO_4$, filtered, evaporated and chromatographed on silica gel, using 4:1 chloroform-ethyl acetate, resulting in the compound, 7-(p-nitrobenzylideneamino)-7-acetoxy-cephalosporanic acid benzhydryl ester.

In a like manner, using propionyl peroxide and butyryl peroxide, respectively, the compounds 7-(p-nitrobenzylideneamino)-7-propionyloxy-cephalosporanic acid benzhydryl ester, 7-(p-nitrobenzylideneamino)-7-butyryloxycephalosporanic acid benzhydryl ester, respectively, are prepared.

In addition, the 7-alkanoyloxy derivatives of the other imino compounds prepared in Example 2 can be easily synthesized using this reaction.

EXAMPLE 12

7-(p-Nitrobenzylideneamino)-7-Hydroxymethyl-Cephalosporanic Acid Benzhydryl Ester A gentle stream of nitrogen is passed into a half-dram vial containing 60 mg. of benzhydryl 7-(p-nitrobenzylideneamino)-cephalosporanate prepared as in Example 2, and after a few minutes 0.3 ml. of N,N-dimethylformamide is added. The nitrogen stream is continued, bubbling through the greenish-brown solution for about 30 seconds, and then a stream of formaldehyde gas in nitrogen, generated by heating 15 mg. of paraformaldehyde in a nitrogen stream, is passed through. The resultant solution is evaporated to a gum under high vacuum. The gum is flushed by dissolving it in a small volume of chloroform and again evaporating to a gum under high vacuum. The product exhibits an ir spectrum with hydroxy, β-lactam, and ester absorption. The nmr spectrum in $CDCl_3$ shows the expected singlet for the benzylidene proton, and new absorption associated with the hydroxymethyl group. The observed peaks are at 517 (1H); 486; 478; 467; 458 (4H); 431 (10H); 407 (1H); 305 (1H); 300; 288; 282; 268 (2H); 240 (2H); 222; 204; 198; 180 (2H); 116 (3H); expressed in cps downfield of tms. The product is identified as 7-(p-nitrobenzylideneamino)-7-hydroxymethyl-cephalosporanic acid benzhydryl ester.

The 7-(α-alkyl)-hydroxymethyl derivatives are made in a similar process. For instance, acetaldehyde, propionaldehyde, and isobutyraldehyde, respectively, can be used to prepare 7-(p-nitrobenzylideneamino)-7-(α-methyl)-hydroxymethyl-cephalosporanic acid benzhydryl ester; 7-(p-nitrobenzylideneamino)-7-(α-ethyl)-hydroxymethyl-cephalosporanic acid benzhydryl ester; and 7-(p-nitrobenzylideneamino)-7-(α-isopropyl)-hydroxymethylcephalosporanic acid benzhydryl ester, respectively.

In addition, the 7-hydroxyalkyl derivatives of the other imino compounds prepared in Example 2 can be synthesized using a similar reaction.

EXAMPLE 13

7-(p-Nitrobenzylideneamino)-7-(β-Cyanoethyl)-Cephalosporanic Acid Benzhydryl Ester A solution of 500 mg. of benzhydryl 7-(p-nitrobenzylideneamino)-cephalosporanate prepared as in Example 2 in a mixture of 2.5 ml. of t-butyl alcohol and 2.5 ml. of acrylonitrile is treated with 20 μl. of N,N-diisopropylethylamine with stirring under nitrogen. The initially green solution turns yellow-orange after stirring ten minutes. It is then concentrated under reduced pressure to 620 mg. of a yellow gummy residue. This residue is chromatographed on a mixture of 48 g. of active, powdered silica gel and 40 g. of powdered diatomateous earth. Elution is carried out with 2% ether in benzene. The desired non-crystalline cyanoethyl adduct is eluted after 2 liters of eluent has passed through the column. The product is identified as 7-(p-nitrobenzylideneamino)-7-(β-cyanoethyl)-cephalosporanic acid benzhydryl ester.

In a like manner, methyl acrylate, nitroethylene, and acrolein, respectively, can be used to prepare 7-(p-nitrobenzylideneamino)-7-($\beta$-carbomethoxyethyl)-cephalosporanic acid benzhydryl ester; 7-(p-nitrobenzylideneamino)-7-($\beta$-nitroethyl)-cephalosporanic acid benzhydryl ester; 7-(p-nitrobenzylideneamino)-7-($\beta$-formylethyl)cephalosporanic acid benzhydryl ester, respectively.

In a like manner, other 7-$\alpha$-hydroxy substituted loweralkylidene compounds of the other imino compounds of Example 2 can be prepared.

EXAMPLE 15

7-(p-Nitrobenzylideneamino)-7-Carboxy-Cephalosporanic Acid Benzhydryl Ester

A solution of 0.5 g. of benzhydryl 7-(p-nitrobenzylideneamino)-cephalosporanate in 5 ml. of tetrahydrofuran is prepared under a nitrogen atmosphere. Carbon dioxide gas is bubbled through the solution until the color disappears. Benzene, 50 ml., is added and the solution washed with aqueous pH 2 phosphate buffer. The benzene solution is dried with $MgSO_4$, filtered and evaporated to afford the product, benzhydryl 7-(p-nitrobenzylideneamino)-7-carboxy-cephalosporanate.

Using carbon disulfide gas or Dry Ice (solid $CO_2$) in the above reaction, the compounds 7-(p-nitrobenzylideneamino)-7-dithiocarboxy-cephalosporanic acid benzhydryl ester or 7-(p-nitrobenzylideneamino)-7-carboxy-cephalosporanic acid, respectively, are prepared.

EXAMPLE 16

Benzyl-6-(p-Nitrobenzylideneamino)Penicillanate

6-Amino-penicillanic acid is converted to the benzyl ester thereof by reacting the parent compound with phenyldiazomethane following the general procedure of Example 1. The benzyl 6-amino-penicillanate is then reacted with p-nitrobenzaldehyde to form benzyl 6-(p-nitrobenzylideneamino)-penicillanate, using the general procedure of Example 2. The compound has a melting point of 90°–92° C. and nmr and ir analysis peaks are correct for the assigned structure.

EXAMPLE 17

Benzyl 6-Methyl-6-(p-Nitrobenzylideneamino)Penicillanate

110 Mg. of benzyl-6-(p-nitrobenzylideneamino)-penicillanate is treated at −78° C. under nitrogen in 4 ml. tetrahydrofuran with 0.109 ml. 2.3 M phenyl lithium, to give the 6-lithio intermediate, having a deep inky blue color. Addition of 0.2 ml. of methyl iodide in 5 ml. dimethylformamide and warming to 25° C. over 20 minutes afforded benzyl-6-methyl-6-(p-nitrobenzylideneamino)penicillanate quantitatively, having the following physical properties. NMR: 1.4, 1.5$\delta$ (gem dimethyl), 1.8$\delta$ (6$\alpha$-methyl), 4.3$\delta$ (3-H), 5.2$\delta$ (OCH$_2\phi$), 5.3$\delta$ (5$\alpha$-H), 8.8$\delta$ (—CH=N), 9 aromatic H at 7.3–8.3$\delta$. IR: $\beta$-lactam and ester carbonyls at 5.64 and 5.71$\mu$, respectively.

In a like manner, benzyl 6-ethyl-6-(p-nitrobenzylideneamino)penicillanate, 135 mg., NMR: 1.08$\delta$, t; 2.2$\delta$, q; J=7 Hz (6$\alpha$-ethyl); 1.4, 1.5$\delta$ (gem. dimethyl); 4.37$\delta$ (3-H); 5.21$\delta$ (OCH$_2\phi$); 5.43$\delta$ (5$\alpha$-H); 8.77$\delta$ (CH=N); 7.3–8.3$\delta$ (aromatic H). IR: $\beta$-lactam and ester carbonyls at 5.64 and 5.71$\mu$ is prepared. Other loweralkyl derivatives, etc., can be prepared analogously to the procedure in Example 3.

EXAMPLE 18

Benzyl 6-Methoxy-6-(p-Nitrobenzylideneamino)Penicillanate

After preparing the 6-lithio intermediate as described in Example 17, bis(methyl)peroxide is added. After working up in a procedure similar to Example 4, the compound benzyl 6-methoxy-6-(p-nitrobenzylideneamino)penicillanate is prepared.

Also, benzyl 6-(4-nitrobenzylideneamino)-6-methylthiopenicillanate can also be prepared using methanesulfenyl chloride in reaction with benzyl 6-(4-nitrobenzylideneamino)-penicillanate as in Example 4. The product is obtained (139 mg. from 100 mg. of starting material) having an NMR spectrum showing peaks at 521 (1 H), 492, 484, 476 (4H), 437 (5H), 331 (1H), 309 (2H), 226 (1H), 134 (3H), 91 (3H), 84 (3H) in cps measured downfield from tms.

The other lower alkoxy and lower alkyl thio derivatives can be prepared using the same procedures.

EXAMPLE 19

Benzyl 6-Chloro-6-(p-Nitrobenzylideneamino)Penicillanate

The starting material benzyl 6-(p-nitrobenzylideneamino)penicillanate, 110 mg., is dissolved in 5 ml. tetrahydrofuran at −78° C. under nitrogen. At −78° C., first 0.109 ml. phenyl lithium and then 0.10 ml. t-butyl hypochlorite is added. The inky blue anion is quenched to a medium pale brown color. After 25 seconds, 1 ml. THF containing 0.1 ml. water and 0.1 ml. AcOH is added, followed by 100 ml. benzene. Most of the solvent is evaporated in vacuo, 50 ml. benzene added and the solution washed with aqueous pH 2 phosphate, water, and aqueous pH 8 phosphate. After drying with $MgSO_4$, filtration and evaporation of the solvent, the residue benzyl 6-chloro-6-(p-nitrobenzylideneamino)penicillanate, weighs 126 mg. NMR: 1.4, 1.5$\delta$ (gem. dimethyl), 4.6$\delta$ (3-H), 5.2$\delta$ (OCH$_2\phi$), 5.8$\delta$ (5-H), 7.3–8.3$\delta$ (aromatic H), 8.8$\delta$ (CH=N). IR: 5.58$\mu$ ($\beta$-lactam), 5.72$\mu$ (ester).

The compound, benzyl 6-bromo-6-benzylideneamino-penicillanate is prepared in the following way:

Benzyl 6-amino-penicillanic acid (3 g., 0.01 mole) is dissolved in 200 ml. of benzene, 1.06 g. (0.01 mole) benzaldehyde is added and the benzene is slowly distilled out until the volume of the solution is 50 ml. The remaining solvent is removed under reduced pressure. The residue is taken up in ether 30 ml. and the solution allowed to stand in the refrigerator overnight. A small amount of an insoluble impurity separates out which is filtered off. The filtrate is evaporated to give 3.5 g. of benzyl 6-benzylideneamino penicillanate. Then 0.394 grams of the latter compound, benzyl 6-benzylideneamino-penicillanate is dissolved in 15 ml. of anhydrous THF under nitrogen and cooled to −78° C., 0.5 ml. of a 2.3 M solution of phenyl lithium is added over 30 seconds. The reaction mixture is stirred for 5 minutes. 0.2 Grams of N-bromosuccinimide in 3 ml. of anhydrous THF is then added. The cooling bath is removed and the reaction mixture is allowed to come to 0° C. The solvent is removed under reduced pressure and the residue is taken up in methylene chloride, 30 ml., and washed once with pH 7 phosphate buffer and then with water, dried and evaporated to a volume of about 10 ml. The compound in solution is benzyl 6- bromo-6-benzylideneamino-penicillanate. This can be converted directly to benzyl 6-methoxy-6-benzylideneamino-penicillanate, using the following procedure:

0.200 Grams of silver oxide is suspended in 20 ml. of methanol. The 10 ml. solution of the bromo benzylideneamino compound obtained above is added dropwise over 10 minutes to the silver oxide suspension. The reaction mixture is stirred for another 15 minutes. The silver salts are filtered off and the filtrate is evaporated and the residue taken up in benzene and washed twice, with pH 7 phosphate buffer, then dried and evaporated to give 0.412 g. of the benzyl 6-methoxy-6-benzylideneamino-penicillanate as a brownish red oil.

ir 5.61$\mu$ ($\beta$-lactam), 5.72 (ester), 6.09 (C=N); nmr 8.45$\delta$ (C$\underline{H}$=N), 5.57$\delta$ (5H), 5.17$\delta$ (C$\underline{H}_2$-C$_6$H$_5$), 3.53$\delta$ (O-CH$_3$), 1.57$\delta$ and 1.39$\delta$ (gem. dimethyl).

The other halo derivatives can be prepared as in Example 8.

EXAMPLE 20

Benzyl 6-Carbomethoxy-6-(p-Nitrobenzylideneamino)Penicillanate

The general procedure described in Example 6 is followed. Benzyl 6-(p-nitrobenzylideneamino)penicillanate (9.5 g.) is dissolved in 95 ml. of acetonitrile.

2.99 Ml. of N,N-diisopropylethylamine is added generating an emerald green color. This is immediately followed by addition of 13.4 ml. of freshly distilled methyl chloroformate then stirred until green color changes to brown (~5 min.). The reaction is quenched by cooling in ice/H$_2$O and adding 13.4 ml. pyridine dropwise, followed by 5 ml. water. After gas evolution has ceased, the reaction is extracted with ethyl acetate, washed with water and saturated sodium chloride, then dried over MgSO$_4$ and evaporated to dryness yielding 11 gm. of crude oil.

Crude material is chromatographed on 300 gm. silica gel packed in benzene. The product benzyl 6-carbomethoxy-6-(p-nitrobenzylideneamino)penicillanate is collected in 10% ether/benzene and obtained as 4.6 gm. M.I.=497 as analyzed by TLC and NMR.

The compound benzyl 6-carbobenzoxy-6-(p-nitrobenzylideneamino)penicillanate can also be prepared by reacting benzyl chloroformate with benzyl 6-(p-nitrobenzylideneamino)penicillanate. 562 Mg. of the product are obtained from 1.0 g. of starting material. Identity is confirmed using NMR.

The other analogous products described in Example 6 can be prepared in the penicillin series following the processes described.

EXAMPLE 21

Benzyl 6-Hydroxymethyl-6-(p-Nitrobenzylideneamino)-Penicillanate

The compound benzyl 6-hydroxymethyl-6-aminopenicillanate is prepared as follows:

In a half dram vial are placed 200 mg. of benzyl 6-(p-nitrobenzylideneamino)penicillanate and 0.5 ml. of N,N-dimethylformamide. A stream of nitrogen is passed briefly through the resulting emerald green solution, followed by a stream of formaldehyde gas in nitrogen generated by heating 50 mg. of paraformaldehyde in a nitrogen stream which is then passed into the Schiff's base solution. The green color is rapidly discharged, to give an orange to yellow solution, which is evaporated to a gum under high vacuum, and flushed twice by dissolving it in a few drops of chloroform and again evaporating to a gum. The resultant material is purified by preparative tlc on a 1000$\mu$ silica gel plate with fluorescent indicator, using 20% ethyl acetate in benzene. The yellow band which shows a dark band under either long or short uv light, and which is usually preceded by a deep yellow (visible light) band, is removed and eluted with ethyl acetate. The ir (CHCl$_3$) shows OH (2.8–3.1$\mu$), $\beta$-lactam (5.65$\mu$) and ester (5.72$\mu$) to be present and the nmr shows the benzylidene and C$_5$-protons as sharp singlets at 532 and 338 ppm downfield from tms in CDCl$_3$. A yield of about 40% of benzyl 6-(4-nitrobenzylideneamino)-6-hydroxymethyl-penicillanate is obtained.

The other derivatives of the cephalosporins found in Examples 3–15 can obviously be prepared in the penicillin series using the processes described therein.

EXAMPLE 22

Regeneration of 7-Amino from 7-Imino Using Products Of Examples 3–21

The regeneration of the 7-amino functionality of all the products produced in the above Examples is accomplished by reacting approximately equimolar amounts of those compounds with aniline hydrochloride in methanol, at room temperature, mixing for from 1 to 24 hours. Other lower alkanols can be used, suitably ethanol. The ethanol is removed in vacuo (about 0.1 mm pressure). The residue is then covered with diethylether. After about one hour has elapsed, the residue crystallizes. The crystals are triturated with ether, filtered and washed several times, followed by addition to 10 ml. of an aqueous (pH=8) phosphate buffer. This mixture is then extracted three times with ether. The ether extracts are dried with MgSO$_4$, filtered, evaporated, and chromatographed on silica gel. The eluate is 4:1 chloroform-ethyl acetate. The 7-amino product is then removed and identified.

EXAMPLE 23

Regeneration of 7-Amino from 7-Imino Using Products Of Examples 3–21

Another method of regeneration of the 7-amino functionality of all the products produced in Examples 3–21 is accomplished by reacting 2,4-dinitrophenylhydrazine with the compound in the presence of an alcoholic solvent and acid. Specific examples follow for selected compounds. The rest of the compounds can be treated as in these examples.

A. Benzhydryl 7-Methoxy-7-Aminocephalosporanate

100 Mg. of powdered 2,4-dinitrophenylhydrazine, 85.5 mg. of p-toluenesulfonic acid monohydrate, and 3 ml. of absolute ethanol are stirred for 30 minutes. To this is added a solution of 304 mg. of benzhydryl 7-methoxy-7-(p-nitrobenzylideneamino)cephalosporanate in 3 ml. of ethanol and 0.5 ml. of methylene chloride. The mixture is stirred for 30 minutes, filtered and after the filter cake has been thoroughly washed with ethanol, the filtrates are evaporated under reduced pressure at or below ambient temperature. The resultant solid is washed several times with ether and dried in a nitrogen stream. This solid is the benzhydryl 7-methoxy-7-amino-7-aminocephalosporanate tosylate salt.

The tosylate salt is converted to the free amine using the following procedure:

A mixture of 3.5 ml. of ether, 0.5 ml. of ethyl acetate, 2 ml. of water and 22 mg. of dipotassium hydrogen phosphate is prepared. To this is added 100 mg. of benzhydryl 7-methoxy-7-aminocephalosporanate tosylate salt and the mixture is shaken vigorously for several minutes. After phase separation the aqueous phase is again extracted with ether, the combined organic phases are dried with anhydrous magnesium sulfate, and evaporated to a gum under reduced pressure. The product is flushed several times by dissolving it in a small volume of chloroform and again evaporating to a gum under high vacuum. The product so obtained exhibits ir and nmr spectra consistent with the assigned structure for benzhydryl-7-methoxy-7-aminocephalosporanate.

B. Benzhydryl-7-Methyl-7-Aminocephalosporanate

109 Mg. of powdered 2,4-dinitrophenylhydrazine, 106 mg. of p-toluenesulfonic acid monohydrate, and 10 ml. of absolute ethanol are stirred for 30 minutes. To this is added a solution of 300 mg. of benzhydryl-7-methyl-7-(4-nitrobenzylideneamino)cephalosporanate in 3 ml. of ethanol. The mixture is stirred for 30 minutes, filtered and after the filter cake has been thoroughly washed with ethanol, the filtrates are evaporated under reduced pressure at or below ambient temperature.

The residue is the benzhydryl-7-methyl-7-aminocephalosporanate tosylate salt which is converted by the below procedure to the free base, having the following characterization: NMR: $1.6\delta$ ($7\alpha$-methyl), $1.95\delta$ (acetyl), 3.05, 3.35, 3.4, $3.7\delta$ ($SCH_2$), 4.5$\delta$, 4.72, 4.85, $5.07\delta$ ($CH_2OAc$), $4.6\delta$ ($6\alpha$-H), $6.86\delta$ ($CH\phi_2$), $7.3\delta$ (aromatic). IR: $\beta$-lactam and ester carbonyls at 5.63 and $5.76\mu$ respectively. MS: 452, 382, 285.

The tosylate salt is converted to the free amine using the following procedure:

A mixture of 3.5 ml. of ether, 0.5 ml. of ethyl acetate, 2 ml. of water and 22 mg. of dipotassium hydrogen phosphate is prepared. To this is added 100 mg. of benzhydryl 7-hydroxymethyl-7-aminocephalosporanate tosylate salt and the mixture is shaken vigorously for several minutes. After phase separation the aqueous phase is again extracted with ether, the combined organic phases are dried with anhydrous magnesium sulfate, and evaporated to a gum under reduced pressure. The product is flushed several times by dissolving it in a small volume of chloroform and evaporating to a gum under high vacuum. The product so obtained exhibits ir and nmr spectra as shown above.

C. Benzhydryl 7-Hydroxymethyl-7-Aminocephalosporanate

A mixture of 100 mg. of powdered 2,4-dinitrophenyl hydrazine, 85.5 mg. of p-toluene sulfonic acid monohydrate, and 3 ml. of absolute ethanol are stirred for 30 minutes. To this is added a solution of 304 mg. of benzhydryl 7-hydroxymethyl-7-(4-nitrobenzylideneamino)-cephalosporanate in 3 ml. of ethanol and 0.5 ml. of methylene chloride. The mixture is stirred for 30 minutes, filtered, and after the filter cake has been thoroughly washed with ethanol, the filtrates are evaporated under reduced pressure at or below ambient temperature. The resultant gum exhibits an ir spectrum ($CHCl_3$ evaporate) with $\beta$-lactam ($5.60\mu$) and ester ($5.76\mu$) absorption, and is identified as benzhydryl 7-hydroxymethyl-7-aminocephalosporanate tosylate salt.

A mixture of 3.5 ml. of ether, 0.5 ml. of ethyl acetate, 2 ml of water and 22 mg. of dipotassium hydrogen phosphate is prepared. To this is added 100 mg. of benzhydryl 7-hydroxymethyl-7-aminocephalosporanate tosylate salt and the mixture is shaken vigorously for several minutes. After phase separation the aqueous phase is again extracted with ether, the combined organic phases are dried with anhydrous magnesium sulfate, and evaporated to a gum under reduced pressure. The product is flushed several times by dissolving it in a small volume of chloroform and again evaporating to a gum under high vacuum. The product, benzhydryl 7-hydroxymethyl-7-aminocephalosporanate, is purified by preparative tlc on silica gel using ether acetate (Rf~0.5). It exhibits an nmr spectrum ($CDCl_3$) with peaks at 444 (10H); 421 (1H), 307, 294, 289, 275 (2H), 291 (1H), 235 (2H), 226, 207, 203, 184 (2H), 158 (B, 2H), 120 (3H) expressed in cps downfield from tms. The ir ($CHCl_3$) showed NH-OH (2.8–3.1$\mu$), $\beta$-lactam (5.60$\mu$) and ester (5.74$\mu$) absorption.

D. Benzyl-6-Hydroxymethyl-6-Aminopenicillanate

Using the same general procedures of Steps A, B, and C, the tosylate salt of benzyl 6-hydroxymethyl-6-aminopenicillanate, is recovered. m.p. 168°–169° C., Calcd. for $C_{23}H_{29}N_2O_7S_2$: C, 54.31; H, 5.55; N, 5.51; S, 12.61. Found: C, 54.01; H, 5.59; N, 5.42; S, 12.54. I.R. (Nujol) NH, OH (2.85, 2.99, 3.7–4.3), $\alpha$-lactam (5.63$\mu$), ester (5.77$\mu$). The nmr (DMSO-$d_6$) showed peaks at 454, 446, 431, 422 (4H), 445 (5H), 330 (1H), 314 (2H), 274 (1H), 233 (2H), 138 (3H), 97 (3H), and 83 (3H) expressed in cps downfield from tms.

After treating with aqueous dipotassium hydrogen phosphate as in steps A, C, and C, a gum is obtained which is benzyl 6-hydroxymethyl-6-aminopenicillanate. It exhibits an ir (neat) spectrum with NH-OH (2.8–3.4$\mu$), $\beta$-lactam and ester (5.6–5.8$\mu$) absorptions; the nmr spectrum exhibits peaks at (numbers in Hz from internal tms in $CDCl_3$) 449 (5H), 325 (1H), 313 (2H), 268 (1H), 235 (2H), 145 (broad; 2H), 97 (3H), and 86 (3H). It shows essentially one spot on tlc on 250$\mu$ silica plates developed with 50% ethyl acetate in benzene.

E. Benzyl 6-Methyl-6-Aminopenicillanate

Using the same procedures as above, benzyl 6-methyl-6-aminopenicillanate, 19.5 mg., is prepared having NMR: 1.42, 1.59$\delta$ (gem. dimethyl), 1.59$\delta$ (6$\alpha$-methyl), 1.85$\delta$ ($NH_2$), 4.44$\delta$ (3-H), 5.20$\delta$ ($OCH_2\phi$), 5.24$\delta$ (5$\alpha$-H), 7.38$\delta$ (aromatic H). IR: $\beta$-lactam and ester carbonyls at 5.61 and 5.71$\mu$, respectively. MS: Strong 320, 292, 250, 130.

F. Benzyl 6-Ethyl-6-Aminopenicillanate

Using the same procedures as above, benzyl 6-ethyl-6-aminopenicillanate, 48 mg., NMR: 1.1$\delta$, t; 2.0$\delta$ q; J=7 HZ (6$\alpha$-ethyl); 1.40, 1.58$\delta$ (gem. dimethyl); 2.0$\delta$ ($NH_2$); 4.44$\delta$ (3-H); 5.20$\delta$ ($OCH_2\phi$); 5.25$\delta$ (5$\alpha$-H); 7.4$\delta$ (aromatic H). IR: 2.95$\mu$ (N-H); $\beta$-lactam and ester carbonyls at 5.65 and 5.72$\mu$, is prepared.

Other compounds which can be prepared using the procedures described in the above Examples are listed herein. The ester is prepared in all cases; specifically, the benzyl ester is prepared in the penicillanic acid series. Either the benzhydryl or the trichloroethyl esters are prepared in the cephalosporanic acid series.

7-amino-7-methyl-cephalosporanic acid
7-amino-7-ethyl-cephalosporanic acid
7-amino-7-propyl-cephalosporanic acid 7-amino-7-methoxy-cephalosporanic acid
7-amino-7-ethoxy-cephalosporanic acid
7-amino-7-butoxy-cephalosporanic acid
7-amino-7-methylthio-cephalosporanic acid
7-amino-7-ethylthio-cephalosporanic acid
7-amino-7-isopropylthio-cephalosporanic acid
7-amino-7-acetyl-cephalosporanic acid
7-amino-7-propionyl-cephalosporanic acid
7-amino-7-trifluoromethoxy-cephalosporanic acid
7-amino-7-trifluoromethylthio-cephalosporanic acid
7-amino-7-chloro-cephalosporanic acid
7-amino-7-bromo-cephalosporanic acid
7-amino-7-fluoro-cephalosporanic acid
7-amino-7-difluoromethyl-cephalosporanic acid
7-amino-7-acetoxy-cephalosporanic acid
7-amino-7-propionyloxy-cephalosporanic acid
7-amino-7-hydroxymethyl-cephalosporanic acid
7-amino-7-($\alpha$-methyl)-hydroxymethyl-cephalosporanic acid
7-amino-7-($\alpha$-isopropyl)-hydroxymethyl-cephalosporanic acid
7-amino-7-($\beta$-cyanoethyl)-cephalosporanic acid
7-amino-7-($\beta$-nitroethyl)-cephalosporanic acid
7-amino-7-($\beta$-formylethyl)-cephalosporanic acid
7-amino-7-allyl-cephalosporanic acid
7-amino-7-benzyl-cephalosporanic acid
7-amino-7-cyano-cephalosporanic acid
7-amino-7-nitroso-cephalosporanic acid
7-amino-7-carbamoyl-cephalosporanic acid
7-amino-7-carboethoxy-cephalosporanic acid
7-amino-7-sulfo-cephalosporanic acid
7-amino-7-sulfamoyl-cephalosporanic acid
7-amino-7-methylsulfo-cephalosporanic acid
7-amino-7-phospho-cephalosporanic acid
7-amino-7-nitro-cephalosporanic acid
7-amino-7-carboxy-cephalosporanic acid
7-amino-7-dithiocarboxy-cephalosporanic acid
7-amino-7-dimethylaminomethyl-cephalosporanic acid
7-amino-7-methyl-3-methyldecephalosporanic acid
7-amino-7-ethyl-3-chloromethyldecephalosporanic acid
7-amino-7-propyl-3-carbamoyloxymethyldecephalosporanic acid
7-amino-7-methoxy-3-methyldecephalosporanic acid
7-amino-7-ethoxy-3-chloromethyldecephalosporanic acid
7-amino-7-butoxy-3-carbamoyloxymethyldecephalosporanic acid
7-amino-7-methylthio-3-methyldecephalosporanic acid
7-amino-7-ethylthio-3-chloromethyldecephalosporanic acid
7-amino-7-isopropylthio-3-carbamoyloxydecephalosporanic acid
7-amino-7-acetyl-3-methyldecephalosporanic acid
7-amino-7-propionyl-3-chloromethyldecephalosporanic acid
7-amino-7-trifluoromethoxy-3-methyldecephalosporanic acid
7-amino-7-trifluoromethylthio-3-methyldecephalosporanic acid
7-amino-7-chloro-3-methyldecephalosporanic acid
7-amino-7-bromo-3-carbamoyloxymethyldecephalosporanic acid
7-amino-7-fluoro-3-carbamoyloxymethyldecephalosporanic acid
7-amino-7-difluoromethyl-3-methyldecephalosporanic acid
7-amino-7-acetoxy-3-methyldecephalosporanic acid
7-amino-7-propionyloxy-3-carbamoyloxymethyldecephalosporanic acid
7-amino-7-hydroxymethyl-3-methyldecephalosporanic acid
7-amino-7-($\alpha$-methyl)-hydroxymethyl-3-methyldecephalosporanic acid
7-amino-7-($\alpha$-isopropyl)-hydroxymethyl-3-carbamoyloxymethyldecephalosporanic acid
7-amino-7-($\beta$-cyanoethyl)-3-methyldecephalosporanic acid
7-amino-7-($\beta$-nitroethyl)-3-methyldecephalosporanic acid
7-amino-7-($\beta$-formylethyl)-3-carbamoyloxymethyldecephalosporanic acid
7-amino-7-allyl-3-chloromethyldecephalosporanic acid
7-amino-7-benzyl-3-methyldecephalosporanic acid
7-amino-7-cyano-3-carbamoyloxymethyldecephalosporanic acid
7-amino-7-nitroso-3-chloromethyldecephalosporanic acid
7-amino-7-carbamoyl-3-methyldecephalosporanic acid
7-amino-7-carboethoxy-3-chloromethyldecephalosporanic acid
7-amino-7-sulfo-3-carbamoyloxymethyldecephalosporanic acid
7-amino-7-sulfamoyl-3-chloromethyldecephalosporanic acid
7-amino-7-methylsulfo-3-methyldecephalosporanic acid
7-amino-7-phospho-3-carbamoyloxymethyldecephalosporanic acid
7-amino-7-nitro-3-methyldecephalosporanic acid
7-amino-7-carboxy-3-chloromethyldecephalosporanic acid
7-amino-7-dithiocarboxy-3-carbamoyloxymethyldecephalosporanic acid
7-amino-7-dimethylaminomethyl-3-methyldecephalosporanic acid
6-amino-6-propyl-penicillanic acid
6-amino-6-methoxy-penicillanic acid
6-amino-6-ethoxy-penicillanic acid
6-amino-6-butoxy-penicillanic acid
6-amino-6-methylthio-penicillanic acid
6-amino-6-propylthio-penicillanic acid
6-amino-6-butylthio-penicillanic acid
6-amino-6-acetyl-penicillanic acid
6-amino-6-propionyl-penicillanic acid
6-amino-6-($\beta$-cyanoethyl)-penicillanic acid
6-amino-6-($\beta$-nitroethyl)-penicillanic acid
6-amino-6-($\beta$-formylethyl)-penicillanic acid
6-amino-6-allyl-penicillanic acid
6-amino-6-benzyl-penicillanic acid
6-amino-6-cyano-penicillanic acid
6-amino-6-nitroso-penicillanic acid
6-amino-6-carbamoyl-penicillanic acid
6-amino-6-carboethoxy-penicillanic acid
6-amino-6-sulfo-penicillanic acid
6-amino-6-sulfamoyl-penicillanic acid
6-amino-6-methylsulfo-penicillanic acid
6-amino-6-phospho-penicillanic acid
6-amino-6-nitro-penicillanic acid
6-amino-6-carboxy-penicillanic acid
6-amino-6-dithiocarboxy-penicillanic acid
6-amino-6-dimethylaminomethyl-penicillanic acid
6-amino-6-trifluoromethoxy-penicillanic acid
6-amino-6-trifluoromethylthio-penicillanic acid
6-amino-6-chloro-penicillanic acid
6-amino-6-bromo-penicillanic acid
6-amino-6-fluoro-penicillanic acid 6-amino-6-difluoromethyl-penicillanic acid
6-amino-6-acetoxy-penicillanic acid
6-amino-6-propionyloxy-penicillanic acid
6-amino-6-hydroxymethyl-penicillanic acid
6-amino-6-(α-methyl)-hydroxymethyl-penicillanic acid
6-amino-6-(α-isopropyl)-hydroxymethyl-penicillanic acid

EXAMPLE 24

Preparation of Amido Derivatives of Example 23

The 7-amino or 6-amino compounds prepared in the previous Example are further reacted to produce superior antibacterial agents. One highly active group at 7 (or 6) is 7-(or 6-)-(2-thienylacetamido), prepared in the following manner.

Approximately equimolar amounts of the 7-amino compound and thienyl acetyl chloride are reacted in solution. Methylene chloride containing a small amount of pyridine is used as the solvent. For instance, when benzhydryl 7-amino-7-methyl-cephalosporanate is used, 452 mg are reacted with 161 mg. thienyl acetyl chloride in 25 ml. of methylene chloride containing 0.5 ml. pyridine. The reaction mixture is held at 0° C. for 15–60 minutes and then raised to room temperature and held an additional 15–60 minutes. The mixture is then washed with water, dilute phosphoric acid (buffered to pH 2), water, and dilute sodium bicarbonate. After drying with $MgSO_4$, the solution is filtered and evaporated. The crude solid is purified by chromatography on silica gel, and eluted using, for instance, 4:1 chloroform-ethyl acetate. The product prepared is the 7-(2-thienylacetamido)-7-R-(methyl)-cephalosporanic acid benzhydryl ester. This latter can be hydrolyzed to the acid by treating for 5–20 minutes at 0°–10° C. with anisole and trifluoroacetic acid. (For instance, 300 mg. of compound in 0.5 ml. of anisole and 2.5 ml. of trifluoroacetic acid.) The resulting mixture is evaporated at reduced pressure and flushed twice with anisole. The residue is dissolved in methylene chloride and extracted with 5% sodium bicarbonate solution. The aqueous solution is adjusted to pH 1.8 with 5% phosphoric acid and extracted with ethyl acetate. The organic solution is dried and evaporated to yield the pure 7-(2-thienylacetamido)-7-R-(methyl)-cephalosporanic acid.

In a like manner, using benzyl 6-amino-6-methyl penicillanate in reaction with thienyl acetyl chloride, the product, 6-(2-thienylacetamido)-6-methylpenicillanic acid is recovered.

This general procedure must be slightly modified when the substituent at 7- (or 6-) is hydroxy methyl. For example, to prepare benzyl 6-hydroxymethyl-6-phenoxyacetamidopenicillanate, benzyl 6-hydroxymethyl-6-aminopenicillanate, obtained from 1.2 g. of tosylate salt, is cooled to 0° C. in 5 ml. of methylene chloride and stirred vigorously with 820 mg. of $K_2HPO_4$ in 15 ml. of water while 440 mg. of phenoxy-acetyl chloride in 10 ml. of dry methylene chloride is added dropwise over a one minute period. After vigorous stirring at 0° C. for another 15 minutes, the phases are separated and the aqueous phase is again extracted with methylene chloride and after drying the combined organic phases with magnesium sulfate, the solvent is removed at reduced pressure to give 1.16 g. of crude product which is purified by chromatography on 35 g. silica gel packed in chloroform. Fractions 1–12 are 20 ml. chloroform, 13 and 14 are 30 ml. of 1% ethyl acetate in chloroform while 15 to 21 are 50 ml. of 2.5% ethyl acetate. Evaluation of the fractions by tlc leads to combination of fractions 5–17 to give 676 mg. of purified material. The ir spectrum ($CHCl_3$) shows NH-OH (2.8–3.1μ), β-lactam (5.62μ), ester (5.73μ) and amide (5.96μ) absorption while the nmr ($CDCl_3$) shows peaks at 452-408 (complex 11H; major peaks at 442 and 421), 338 (1H), 312 (2H), 272 (2H), 268 (1H), 253 (2H), 86 (3H) and 82 (3H) expressed in cps downfield from tms. The mass spectrum also showed the desired molecular ion at m/e 470.

The product prepared is the 6-phenoxyacetamido-6-hydroxymethyl-penicillanic acid benzyl ester. This can be converted to the acid by catalytic hydrogenolysis. For instance, 100 mg. of compound in 50 ml. of ethanol-water (2:1), containing one equivalent of sodium bicarbonate to which 100 mg. of 10% Pd/C catalyst is added, is prepared. The resulting mixture is shaken in a hydrogen atmosphere (40 psi) for one hour. After filtration and lyophyllization, the product, sodium 6α-hydroxymethyl-6β-phenoxyacetamidopenicillanate, is obtained.

EXAMPLE 25

A. Benzyl 6-(N-p-Nitrobenzyl-N-oxy)Imino Penicillanate and 6,6'-Linked Dimer of benzyl 6-(p-Nitrobenzylideneamino) Penicillanate Benzyl 6-(p-nitrobenzylideneamino)penicillanate, 439 mg., in 16 ml. THF at −78° C. under nitrogen, is treated with 0.500 ml. 2.0 M phenyl lithium, forming the activated 6-lithio intermediate. The temperature is raised to 0° C. and dry oxygen is passed through the mixture with rapid stirring for ten minutes. The color changes from inky blue to pale maroon. Benzene (50 ml.) and 0.1 ml. acetic acid are added, and the mixture is washed with water three times, pH 8 phosphate buffer, and water. After drying with $MgSO_4$, filtration, and evaporation of the solvent, a mixture of products is obtained, 302 mg. After preparative layer chromatography on silica gel, developing with 4:1 $CHCl_3$-EtOAc, the two pure products are separated and isolated. The benzyl 6-(N-p-nitrobenzyl-N-oxy)imino penicillanate has the following NMR: (60 Hz, $CDCl_3$): 1.37δ, s; 1.44δ, s (gem. dimethyls); 4.44, 4.70, 4.76, 5.00δ (ArC$\underline{H}_2$N(O)=); 4.83δ (3-H); 5.15δ, s (φC$\underline{H}_2$O—); 6.45δ, s (5-H); 7.3δ, s (Phenyl); 7.32, 7.47, 8.06, 8.21δ (p-$O_2$Nφ—). IR: 5.68μ (β-lactam), 5.72μ (ester). The NMR of the 6,6'-linked dimer of benzyl 6-(p-nitrobenzylideneamino)penicillanate is (60 Hz, $CDCl_3$): 1.41. 1.51δ (gem. dimethyls); 4.36δ, s (3-H); 5.15δ, s (φC$\underline{H}_2$O—); 5.96δ, s (5-H); 7.16δ, s (phenyl); 7.88, 8.03, 8.16, 8.31δ (p-$O_2$Nφ—); 8.79δ, s (—C$\underline{H}$=N—). IR: 5.63μ (β-lactam); 5.73μ (ester).

B. 6,6'-Linked Dimer of Benzyl 6-Aminopenicillanate

The 6,6'-linked dimer of benzyl 6-(p-nitrobenzylideneaminopenicillanate, 98 mg., is stirred for one hour in 10 ml. ethanol with the salt (pre-formed in ethanol for 30 minutes) of 109 mg. 2,4-dinitrophenylhydrazine and 105 mg p-toluenesulfonic acid. The mixture is filtered, evaporated, treated with pH 8 aqueous phosphate buffer, and extracted 3 times with ether. The ether is dried with $MgSO_4$, filtered and evaporated, affording 92 mg. of compound, 6,6'-linked dimer of benzyl 6-aminopenicillanate, NMR (60 Hz, $CDCl_3$): 1.39, 1.49δ (gem. dimethyls); 4.48δ, s (3-H); 5.19δ, s (φC$\underline{H}_2$O); 5.64δ, s (5-H); 7.37δ, s (phenyl); 2.1δ, broad (amino). IR: 5.61μ (β-lactam); 5.72μ (ester). MS: 610, 361, 346, 344, 306, 250.

C. 6,6'-Linked Dimer of Benzyl 6-(2-Phenylacetamido) Penicillanate

The 6,6'-linked dimer of benzyl 6-aminopenicillanate, 60 mg., is treated in 5 ml. CH₂Cl₂ with 60λ pyridine and 25λ phenylacetyl chloride for one hour at 25° C. The solvent is partially evaporated, 25 ml. benzene is added, and the solution is washed with pH 2 aqueous phosphate, water, and pH 8 aqueous phosphate. After drying with MgSO, filtration, and evaporation of the solvent, the compound 6,6'-linked dimer of benzyl 6-(2-phenylacetamido)penicillanate, is obtained, which is purified by chromatography on silica gel, eluting with 10:1 CHCl₃-EtOAc.

D. 6,6'-Linked Dimer of Sodium 6-(2-Phenylacetamido) Penicillanate

The 6,6'-linked dimer of benzyl 6-(2-phenylacetamidopenicillanate, 50 mg., is hydrogenated at 40 psi for one hour in 5 ml. methanol and 1.2 ml. water with 50 mg. 10% Pd/C and 9.6 mg. NaHCO₃. The mixture is filtered and lyophilized, affording 40 mg. of compound, 6,6'-linked dimer of sodium 6-(2-phenylacetamido)-penicillanate.

E. 7,7'-Linked Dimer of Sodium 7-(2-Thienylacetamido)-3-Carbamoyloxymethylcephalosporanate Using the same steps described above in A-D, with the starting material, the benzhydryl 7-(p-nitrobenzylideneamino)-3-carbamoyloxymethyldecephalosporanate, the products, the 7,7'-linked dimer of either benzhydryl or sodium 7-(2-thienylacetamido)-3-carbamoyloxymethylcephalosporanate is prepared (using thienylacetyl chloride in the reaction in step C). In addition, the nitrone, benzhydryl 7-(N-p-nitrobenzyl-N-oxy)imino-3-carbamoyloxymethyldecephalosporanate is isolated at step A.

EXAMPLE 26

Trichloroethyl-6-(p-Chlorobenzylideneamino)Penicillanate

The potassium salt of penicillin G (85 g.) is suspended in one liter of dry acetone containing 27 ml. pyridine. The slurry is cooled to 0° C., and the trichloroethyl-chloroformate (31.6 ml.) in 300 ml. acetone is added dropwise while stirring and maintaining at a temperature 0°–5° C. After stirring overnight, evaporation and recrystallization, a 49.3% yield of the trichloroethyl ester of penicillin G is recovered. 64.4 G. of the latter is then dissolved in 120 ml. of chloroform. This solution is added to a previously prepared mixture of 252 ml. chloroform, 42.0 g. PCl₅, and 45.2 ml. of quinoline held at −15° C. The addition is mildly exothermic, but the temperature is maintained at −15° C. by cooling. After slight aging, n-propanol (120 ml.) is added over 15 minutes at 0° C. Then a mixture of 21.5% aqueous sodium chloride and 38.4 ml. of water are added on a five minute period. The two-phase system is kept at −10° C. while 280 ml. hexane is added, followed by 760 ml. addition of hexane. Crystallization occurred. The product, trichloroethyl-6-amino penicillanate, is obtained in 82.3% yield.

7.0 G. of trichloroethyl-6-amino penicillanate is slurried in 50 ml. benzene; 3.0 ml. of triethylamine is then added. After filtering, the solid cake is washed with 100 ml. benzene. To the combined filtrate and wash is added 3.36 g. p-chlorobenzaldehyde. 9.0 G. of molecular sieves are also added. After filtering following aging of 1½ hours, the residue is dissolved in hexane and recrystallized. 7.6 G. of product (69% yield) is obtained. IR and NMR indicates that trichloroethyl-6-(p-chlorobenzylideneamino)penicillanate is prepared.

The product from this example can be reacted following the procedures in Examples 17–21.

What is claimed is:

1. The compound having the formula:

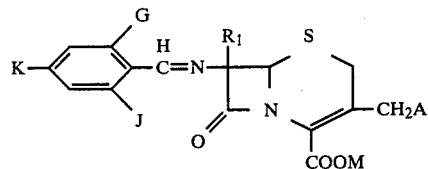

wherein M is benzyl, benzhydryl, trichloroethyl, methoxybenzyl; A is hydrogen, acetoxy, or pyridinium; each of G, K and J are hydrogen, halo, or nitro; and R₁ is loweralkylthio.

2. The compound according to claim 1 wherein R₁ is methylthio; each of G, K and J are hydrogen; and A is hydrogen or acetoxy.

3. The compound according to claim 2 wherein A is hydrogen.

4. The compound according to claim 2 wherein A is acetoxy.

5. A compound of the formula:

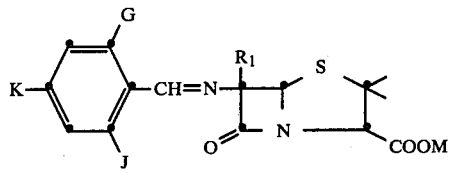

wherein:
M is hydrogen, benzyl, benzhydryl or alkali metal;
R₁ is lower alkylthio; and wherein each of K, G, J, are hydrogen, halo or nitro.

6. The compound having the formula:

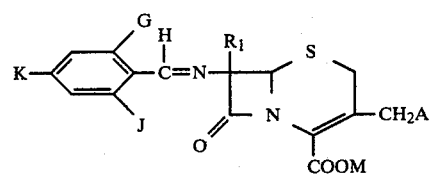

wherein M is benzyl, benzhydryl, trimethylsilyl, trichloroethyl, methoxymethyl, benzoylmethyl, or methoxybenzyl; wherein A is hydrogen, loweralkanoyloxy, carbamoyloxy, thiocarbamoyloxy, N-loweralkylcarbamoyloxy, N-loweralkylthiocarbamoyloxy, N,N-diloweralkylcarbamoyloxy, N,N-diloweralkylthiocarbamoyloxy, pyridinium, alkylpyridinium, halopyridinium, or aminopyridinium;

and wherein each of G, K, and J are hydrogen, halo, nitro, methyl sulfonyl, or cyano;

and R₁ is loweralkanoyl, loweralkoxy, lowerhaloalkoxy, loweralkylthio, lowerhaloalkylthio, halo, loweralkanoyloxy, nitroso, carbamoyl, carboloweralkyoxy, sulfo, sulfamoyl, loweralkylsulfo, phospho, nitro, carboxy, dithiocarboxy, carbobenzoxy, or dimethylaminomethyl.

7. The compound having the formula:

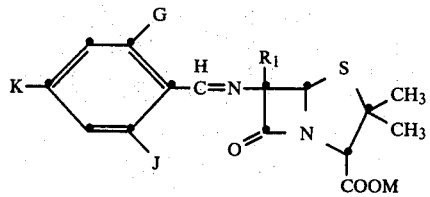

wherein M is benzyl, benzhydryl, trimethylsilyl, trichloroethyl, methoxymethyl, benzoylmethyl, or methoxybenzyl;

and wherein each of G, K, and J are hydrogen, halo, nitro, methyl sulfonyl, or cyano;

and $R_1$ is loweralkanoyl, loweralkoxy, lowerhaloalkoxy, loweralkylthio, lowerhaloalkylthio, halo, loweralkanoyloxy, nitroso, carbamoyl, carboloweralkyoxy, sulfo, sulfamoyl, loweralkylsulfo, phospho, nitro, carboxy, dithiocarboxy, carbobenzoxy, or dimethylaminomethyl.

* * * * *